United States Patent [19]

Fitton

[11] Patent Number: 5,306,626
[45] Date of Patent: Apr. 26, 1994

[54] PROCESS FOR PRODUCTION OF RESTRICTOCIN

[75] Inventor: John E. Fitton, Buxton, United Kingdom

[73] Assignee: Zeneca Limited, London, England

[21] Appl. No.: 32,842

[22] Filed: Mar. 16, 1993

[30] Foreign Application Priority Data

Mar. 16, 1992 [GB] United Kingdom ............... 9205695
Dec. 7, 1992 [GB] United Kingdom ............... 9225541
Jan. 12, 1993 [GB] United Kingdom ............... 9300439

[51] Int. Cl.$^5$ ........................................... C12P 21/02
[52] U.S. Cl. ................................. 435/69.1; 435/849; 935/73
[58] Field of Search ............... 435/69.1, 320.1, 252.3, 435/252.33, 252.8, 849, 199

[56] References Cited

U.S. PATENT DOCUMENTS 3,104,204  9/1963  Olson ................................. 424/117
3,104,208  9/1963  Olson et al. ........................ 435/71.1

FOREIGN PATENT DOCUMENTS 0402544   6/1989  European Pat. Off. .
0466222A1 6/1991  European Pat. Off. .
0524768   1/1993  European Pat. Off. .
3-266986 11/1991  Japan .
2216891A  1/1989  United Kingdom .

OTHER PUBLICATIONS

Lamy et al. Nucleic Acids Res. 19 1001–1006 (1991).
Henze et al. Eur. J. Biochem. 192 127–131 (1990).
Wool, TIBS, "The Mechanism of Action of the Cytotoxic Nuclease α-sarcin and Its Use to Analyse Ribosome Structure", pp. 14–17, (1984).
Miller et al, FEBS Letters, "The Ribosomes of *Aspergillus giganteus* are Sensitive to the Cytotoxic Action of α-sarcin", 229(2):388–390, 1988.
Brigotti at al, Biochem. J., "Effect of α-sarcin and Ribosome-inactivating Proteins on the Interaction of Elongation Factors with Ribosomes", 257:723–727 (1989).
Sanz et al, FEBS Letter, "Sensitivity of Thermoacidophilic Archaebacteria to α-sarcin", 171(1):63–66 (1984).
Endo et al, Biological Chemistry, "The Ribonuclease Activity of the Cytotoxin α-sarcin", 258(4):2662–2667 (1983).
Rodriguez et al, J. Biochemical and Biophysical Research Communications, "Amino Acid Sequence Homologies in *Alfa-Sarcin, Restrictocin* and *Mitogillin*", 108(1):315–321 (1982).
Endo et al, J. Biological Chemistry, "The Site of Action of α-Sarcin on Eukaryotic Ribosomes", 257(15):9054–9062, (1982).
Hobden et al, J. Biochem., "The Mode of Action of Alpha Sarcin and A Novel Assay of the Puromycin Reaction", 170:57–61, (1978).
Schindler et al, Nucleic Acids Research, "Specific Cleavage of Ribosomal RNA Caused by Alpha-Sarcin", 4(4):1097–1111, (1977).

(List continued on next page.)

Primary Examiner—Robert A. Wax
Assistant Examiner—G. Bugaisky
Attorney, Agent, or Firm—Nixon & Vanderhye

[57] ABSTRACT

Methods for recombinant production in procayotic microorganisms such as *E. coli* of ribotoxins such as restrictocin, alpha-sarcin and mitogillin are described. Known methods were relatively low yielding and not cost effective for commercial use such as in the pharmaceutical industry where relatively large quantities of toxin with consistent batch to batch quality may be required for immunotoxin production. Use of recombinant methods of production open up the possibility of making ribotoxin analogues. Toxicity of ribotoxins was recognised as a concern in development of a high yielding cost effective production method. Methods for high yielding intracellular accumulation or secretion of ribotoxins are described. Use of protease deficient strains and other methods of minimising breakdown of ribotoxin by protease are preferred. Vectors and host strains for use in the methods are described.

4 Claims, 3 Drawing Sheets

OTHER PUBLICATIONS

Olson et al, Applied Microbiology, "Alpha Sarcin, a New Antitumor Agent" 13(3):314-321, 322-326, (1965).

Sacco et al, J. Biological Chemistry, "The Primary Structure of the Cytotoxin α-Sarcin", 258(9):5811-5818 (1963).

Oka et al, Biochimica et Biophysica Acta, "An Efficient Expression System for a Variant Form of the Cytotoxic Protein α-Sarcin in *Escherichia coli*" 1130:182-183 (1992).

Orlandi et al, J. Cancer Immunol. Immunother, "Immunoconjugate Generation Between the Ribosome Inactivating Protein Restrictocin and an Anti-Human Breast Carcinoma MAB", 26:114-120 (1988).

Lopez-Otin et al, Eur. J. Biochem. "The Primary Structure of the Cytotoxin Restrictocin", 143, (1984), 621-634.

Hartley et al, FEBS Letters, "Single-chain Ribosome Inactivating Proteins from Plants Depurinate *Escherichia coli* 23S Ribosomal RNA", 290(1,2), (1991), 65-68.

Baneyx et al, J. Bacteriology, "In vivo Degradation of Secreted Fusion Proteins by the *Escherichia coli* Outer Membrane Protease OmpT" 172(1), (1990), 491-494.

Fando et al, Eur. J. Biochem., "The Mode of Action of Restrictocin and Mitogillin on Eukaryotic Ribosomes Inhibition of Brain Protein Synthesis, Cleavage and Sequence of the Ribosomal RNA Fragment", 149, (1985), 29-34.

Better et al, Third International Symposium on Immunotoxins, "Generation of Potent Immunoconjugates from Microbially Produced Fab', F(ab')₂ and Antibody-Toxin Gene Fusions", Jun. 19-21, 1992, Orlando, Fla., Abstracts p. 77.

Bernhard et al, Third International Symposium on Immunotoxins, "Enhanced Potency of Antibody Conjugates with Toxin Analogs of Gelonin, Brip and Mitogillin", Jun. 19-21, 1992, Orlando, Fla., Abstracts p. 64.

Sperti et al, Biochemical and Biophysical Research Communications, "Alpha-Sarcin Impairs the N-Glyosidase Activity of Ricin on Ribosomes", 160(2), (1989), 857-861.

Singh et al, Biochem. J., "Effects of Thiolation on the Immunoreactivity of the Ribosome-Inactivating Protein Gelonin", 263, (1989), 417-423.

Meerman et al, Abstracts Papers American Chem. Soc.; 203 (1-3) 1992.

Pozo et al, Biochimica et Biophysica Acta, "Conformational Study of the Antitumor Protein α-sarcin", 953, (1988), 280-288.

Kenealy et al, Abstrs. Papers Am. Chem. Soc. 202, (1991) 1.

Munzo et al, Biochemical and Biophysical Research Communications, 173(2), "Fractionation of the Ribosome Inactivating Protein Preparations with Triazine Dyes", (1990), 554-560.

Moser et al, J. Immunology, "Cloning and Expression of Recombinant *Aspergillus fumigatus* Allergen I/a (rAsp f I/a) With IgE Binding and Type I Skin Test Activity", 149, (1992), 454-460.

Fernandez-Luna et al, J. Biochemistry, "Complete Amino Acid Sequence of the Aspergillus Cytotoxin Mitogillin", 24, (1985), 861-867.

Conde et al, Eur. J. Biochem., "The Aspergillus Toxin Restrictocin is a Suitable Cytotoxic Agent for Generation of Immunoconjugates with Monoclonal Antibodies Directed Against Human Carcinoma Cells", 178, (1989), 795-802.

Canevari, Meeting of UCLA Symposia, Mar. 9-16; 1986; J. Cell Biochem. Suppl. (10 Part B), 1986, p. 77.

Prestle et al, FEBS Letters, "Mechanism and Site of Action of a Ribosome-Inactivating Protein Type 1 from *Dianthus barbatus* which Inactivates *Escherichia coli* Ribosomes", 297, (1992), 250-252.

Yang et al, J. Gen. Microb., "Regulation of Restrictocin Production in *Aspergillus restrictus*", 138, (1992), 1421-1427.

Endo et al, Article 14 in Genetically Engineered Toxins, Arthur E. Frankel—ed. Marcel Dekker Inc. "An Efficient Expression System for α-Sarcin in *Escherichia coli*", (1992), ISBN 08247 84545.

Piatak et al, Genetically Engineered Toxins, Arthur E. Frankel—ed. Marcel Dekker Inc. "Expression of Plant-Derived Ribosome-Inactivating Proteins in Heterologous Systems" (1992), ISBN 08247 84545.

Yang et al, J. Bilogical Chemistry, "Effects of Amino-terminal Extensions and Specific Mutations on the Activity of Restrictocin", 267(24), (1992) 16801-16805.

Lamy et al, Article 13 in Genetically Engineered Toxins, Arthur E. Frankel—ed. Marcel Dekker, Inc., "The Aspergillus Ribonucleolytic Toxins (Ribotoxins)", (1992), ISBN 08247 84545.

Sehnke et al, Appendix in Genetically Engineered Toxins, Arthur E. Frankel—ed., Marcel Dekker Inc., "Primary Amino Acid Sequences of Toxins" (1992), ISBN 08247 84545.

Ramakrishman et al, Annu. Rev. Pharmacol. Toxicol, "Cytotoxic Conjugates Containing Translational Inhibitory Proteins", 32, (1992), 579-621.

Brandhorst, J. Gen. Microb., "Production and Localization of Restrictocin in *Aspergillus restrictus*", 138, (1992), 1429-1435.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCCTCAGCTG CAGCTACTTG GACTTGYATC AAYCARCA           3 8

( 2 ) INFORMATION FOR SEQ ID NO:2:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CACCGACGTC GACTATTATT ARTGRSWRCA CAGNCGCAGR TCRCCYTGRT T    5 1

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

AATTCGAGCT CGCCCGGGGA TCCTGCAGCT ACTTGGACTT G        4 1

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCAAGCTTGG GTTGCAGGTC GACTATTATT AGTGGCTACA CAGTC    4 5

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTTTTCCCAG TCACGAC        1 7

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAGGAAACAG CTATGAC                                       17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

ACGGGAATGG CAAGCTC                                       17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GGTCTGGCTG TGCTTCG                                       17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GAACCAGTGC GGGTAGC                                       17

( 2 ) INFORMATION FOR SEQ ID NO:10:

( i ) SEQUENCE CHARACTERISTICS:
        ( A ) LENGTH: 456 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GCTACTTGGA  CTTGTATCAA  CCAACAGCTG  AATCCCAAGA  CAAACAAATG  GGAAGACAAG    60
CGGCTTCTAT  ACAGTCAAGC  CAAAGCCGAA  AGCAACTCCC  ACCACGCACC  TCTTTCCGAC   120
GGCAAGACCG  GTAGCAGCTA  CCCGCACTGG  TTCACTAACG  GCTACGACGG  GAATGGCAAG   180
CTCATCAAGG  GTCGCACGCC  CATCAAATTC  GGAAAAGCCG  ACTGTGACCG  TCCCCCGAAG   240
CACAGCCAGA  ACGGCATGGG  CAAGGATGAC  CACTACCTGC  TGGAGTTCCC  GACTTTTCCA   300
GATGGCCACG  ACTATAAGTT  TGACTCGAAG  AAACCCAAGG  AAGACCCGGG  CCCAGCGAGG   360
GTCATCTATA  CTTATCCCAA  CAAGGTGTTT  TGCGGCATTG  TGGCCCATCA  GCGGGGGAAT   420
CAAGGCGATC  TGCGACTGTG  TAGCCACTAA  TAATAG                              456
```

( 2 ) INFORMATION FOR SEQ ID NO:11:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CAATCTAGAG GGTATTAATA ATGTTCCCAT TGGAGGATGA TTAAATGGTA C        51

( 2 ) INFORMATION FOR SEQ ID NO:12:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CATTTAATCA TCCTCCAATG GGAACATTAT TAATACCCTC TAGATTGAGC T        51

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CAATAACACA GGAACAGATC TATGGTAC        28

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CATAGATCTG TTCCTGTGTT ATTGAGCT        28

( 2 ) INFORMATION FOR SEQ ID NO:15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CACTAGTTTA GGAAACAGAC CATGGTAC        28

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CATGGTCTGT TTCCTAAACT AGTGAGCT        28

( 2 ) INFORMATION FOR SEQ ID NO:17:

( i ) SEQUENCE CHARACTERISTICS:
        ( A ) LENGTH: 305 base pairs
        ( B ) TYPE: nucleic acid
        ( C ) STRANDEDNESS: double -continued (D) TOPOLOGY: linear (xi) SEQUENCE DESCRIPTION: SEQ ID NO:17:

```
AATTCTGGCA AATATTCTGA AATGAGCTGT TGACAATTAA TCATCGAACT AGTTAACTAG    60
TACGCAGAGC TCACCAGCAA CTGAACGATC TAAAGCCTGC GTCATCCAGG GTGTTGGCGT   120
AACCGAAACT CCGCTGATGA AAGAAGACTC CATCCTGGCT GTTCGCAAAT ACTTCCAGCG   180
TATCACCCTG TACCTGAAAG AGAAGAAATA CAGCCCGTGC GCTTGGGAAG TTGTACGCGC   240
TGAAATCATG AGATCTTTCA GCCTGTCCAC TAACCTGCAA GAATCTCTGC GTAGCAAAGA   300
ATAAG                                                              305
```

(2) INFORMATION FOR SEQ ID NO:18:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:18:

```
Ala Thr Trp Thr Xaa Ile Asn Gln Gln Leu Asn Pro Lys
 1               5                   10
```

(2) INFORMATION FOR SEQ ID NO:19:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:19:

```
Ala Thr Trp Thr Cys Ile Asn Gln Gln Leu Asn Pro Lys
 1               5                   10
```

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:20:

```
ATGAAATACC TATTGCC                                                   17
```

(2) INFORMATION FOR SEQ ID NO:21:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:21:

```
ATGAAATACC TATTGCCTAC GGCAGCCGCT GGATTGTTAT TACTCGCTGC CCAACCAGCG    60
ATGGCCGGC                                                           69
```

PROCESS FOR PRODUCTION OF RESTRICTOCIN

The present invention relates to methods for the intracellular accumulation of a ribotoxin in a procaryotic host, to replicative expression vectors for use in such methods, and to procaryotic host cells transformed with such a replicative expression vector. Another aspect of the invention relates to secretion of a ribotoxin through the cytoplasmic membrane of a procaryotic host.

BACKGROUND

Ribotoxins are potent inhibitors of protein synthesis. They are believed to act as enzymes on the 28S rRNA of the eucaryotic ribosome and can be divided into two classes (Jiminez, A et al., 1985, Ann. Rev Microbiol., 39, 649-672, and Wool, I. G. et al., 1990, in Hill, W. E. et al. (ed.) The Ribosome Structure, Function & Evolution, American Society of Microbiology, Washington DC, 203-214). Restrictocin, mitogillin and α-sarcin belong to the class which cleaves a single phosphodiester bond. Ricin belongs to the other class which cleaves an N-glycosidic linkage between base and ribose. The nucleotide sequence of the restrictocin gene has been described by Lamy, B. & Davies, J. in Nucleic Acids Research, 1991, 19, 1001-1006.

Such toxins may be used for example in the preparation of immunotoxins for cancer therapy. Pharmaceutical applications of toxins require access to relatively large quantities of toxin of a consistent quality. Cost-effective production techniques are of considerable commercial importance. Toxins may be obtained from their natural sources but this is undesirable because of poor yields and batch to batch variability leading to inconsistent product quality and high production cost. Natural sources are unsuitable for production of analogues of toxins which may be required for certain applications.

Genetic engineering techniques may be applied to the production of toxins but in the case of restrictocin, mitogillin and α-sarcin known methods have failed to provide a cost-effective or high yielding production method. Restrictocin expression using recombinant DNA technology has been described by Lamy, B. and Davies, J. (Nucleic Acids Res. (1991) 19(5) p1001-1006. They expressed and secreted restrictocin from *Aspergillus nidulans*, but the level of secretion was low, even lower than that from the natural producer strain, *Aspergillus restrictus*. There have been no reports of restrictocin expression in bacteria, although the related toxin, alpha sarcin, has been expressed in *E. coli* (Henze, P-P, C. et al. (1990) Eur. J. Biochem. 192, p127-131). Again, expression was low, as the protein could not be detected in total cell lysates by Coomassie blue staining of one-dimensional SDS PAGE electrophoretograms.

In both the Henze and Lamy documents expression vectors designed to allow secretion were employed. This allowed the authors to circumvent toxic effects on the host cells. Henze teaches that a secretion system is necessary, even in *E. coli*, to avoid toxic effects on the host cell (see 2nd. paragraph of the Discussion on page 130) and also teaches that the host ribosomes are sensitive in vivo to the expressed toxin (see 7th paragraph of the Discussion on page 130). Lamy teaches that even one free molecule of restrictocin inside an Aspergillus cell may be lethal (see 7th line of the first column on page 1005). Hence known methods teach that if expression vectors designed to give high level intracellular accumulation of restrictocin were used the method would not work due to toxicity of the product leading to cell death.

SUMMARY OF THE INVENTION

The present invention demonstrates that, surprisingly, mature restrictocin can accumulate intracellularly, at high levels, for example within the cytoplasm of *E. coli*. This enables the disadvantages of known methods outlined above to be ameliorated. The present inventors have further demonstrated that restrictocin is highly unstable in *E. coli* and has a short half life of the order of a few minutes. The unexpected instability of restrictocin provides further obstacles to any worker arriving at the present invention from the known methods since even if the teaching of the art was ignored and attempts were made to express restrictocin in conventional bacterial expression systems as an intracellular accumulated product, the attempt would be unsuccessful due to degradation of the product. The worker might therefore conclude that the known teaching was correct and that the lack of success was due to toxicity of the product. The present invention is also directed to secretion systems in procaryotic hosts wherein proteolytic degradation of ribotoxin is ameliorated.

The present invention is thus based on the discovery that biologically active ribotoxin able to cleave a single phosphodiester bond of 28S rRNA in a 60S ribosomal subunit may be obtained by the intracellular accumulation of ribotoxin in a procaryotic host provided the rate of production of the ribotoxin exceeds its rate of degradation. The present invention is also based on the discovery that proteolytic degration of ribotoxin can be ameliorated in secretion systems based on procaryotic hosts.

Thus according to one aspect of the present invention there is provided a method for producing a biologically active ribotoxin able to cleave a single phosphodiester bond of 28S rRNA in a 60S ribosomal subunit which comprises culture of a procaryotic host carrying a vector with a gene for expression of a ribotoxin under control of expression signals compatible with the host wherein on expression of the gene the ribotoxin is accumulated intracellularly.

Preferably the ribotoxin is accumulated intracellularly and produced under any of the following conditions:

a) the host is protease deficient and/or;
b) degradation of the expressed ribotoxin is suppressed by:
   i) protease inhibitors and/or;
   ii) rapid processing after harvesting the host cells and/or;
   iii) processing at chilled temperatures after harvesting the host cells.

Preferably the ribotoxin is accumulated intracellularly and produced under any of the following conditions:

a) the host is protease deficient and/or;
b) degradation of the expressed ribotoxin is suppressed after culture of the procaryotic host by:
   i) protease inhibitors and/or;
   ii) rapid processing and/or;
   iii) processing at chilled temperatures.

The ribotoxin thus accumulated is preferably recovered from the host and if necessary subjected to renaturation whereby to obtain biologically active ribotoxin. Recovery may for example be effected by any convenient method such as lysis and retrieval of released ribotoxin. The ribotoxin obtained may then, if desired, be purified by any convenient method. If the ribotoxin is accumulated as a fusion protein the fusion partner may need to be cleaved from the ribotoxin for activation of the toxin.

It will be appreciated that the ribotoxin may be expressed in 1) soluble form, 2) in soluble form together with inclusion body formation or 3) in the form of inclusion bodies alone; for example within the cytoplasm of the host. Whilst highly toxic ribotoxins may be expressed as inclusion bodies (which are expected to be inactive as toxins due to insolubility) the skilled person would appreciate there would always be residual ribotoxin present in soluble form which would be expected to be toxic to the cell. The residual ribotoxin may, for example, derive from soluble toxin (produced as a direct result of gene expression) before transformation into insoluble inclusion bodies.

Expression and purification of polypeptides expressed in *E. coli* has been reviewed by F. A. O. Marston in Chapter 4 of DNA cloning Vol III, Practical Approach Series, IRL Press, Glover, D. M. (editor), 1987 and; Biochemistry Journal (1986) 240, 1-12. Gene expression technology has been reviewed in Methods in Enzymology, 185, Academic Press, 1990, Edited by D. V. Goeddel. Protein Purifcation techniques have been reviewed in Methods in Enzymology 182, Academic Press, 1990. High level gene expression in *E. coli* has been reviewed by G. Gross in Chimicaoggi, March 1989, 21-29. Fusion tails for the recovery and purification of recombinant proteins has been reviewed by Ford et al in Protein Expression and Purification 2, 95-107 (1991).

Preferably the host is a bacterium, more preferably of the genus *Bacillus, Streptomycetes, Pseudomonas* or *Escherichia* and especially *E. coli*. Preferably the gene for expression of the ribotoxin maximises codon usage selecting for those codons found in highly expressed genes of the host.

According to another aspect of the present invention there is provided a procaryotic replicative expression vector for intracellular expression of a biologically active ribotoxin able to cleave a single phosphodiester bond of 28S rRNA in a 60S ribosomal subunit.

According to another aspect of the present invention there is provided procaryotic host cells transformed with a replicative expression vector as described above. Preferably the host cells are protease deficient.

A preferred microorganism for use in this aspect of the present invention is MSD460 (NCIMB 40469) which is referred to hereinafter.

Further, MSD460 (NCIMB 40469) per se constitutes a further aspect of the present invention. *E. coli* MSD 199 (NCIMB 40468) and *E. coli* MSD 500 (NCIMB 40470) are further aspects of the present invention.

According to another aspect of the present invention there is provided a method for producing a biologically active ribotoxin able to cleave a single phosphodiester bond of 28S rRNA in a 60S ribosomal subunit which comprises culture of a procaryotic host carrying a vector with a gene for expression of a ribotoxin under control of expression signals compatible with the host, the ribotoxin being secreted through the cytoplasmic membrane of the host after gene expression, characterised in that:

a) the host is protease deficient and/or;

degradation of the expressed ribotoxin is suppressed by:

i) protease inhibitors and/or;

ii) rapid processing after harvesting the host cells or supernatant;

iii) processing at chilled temperatures after harvesting the host cells or supernatant.

According to another aspect of the present invention there is provided a method for producing a biologically active ribotoxin able to cleave a single phosphodiester bond of 28S rRNA in a 60S ribosomal subunit which comprises culture of a procaryotic host carrying a vector with a gene for expression of a ribotoxin under control of expression signals compatible with the host, the ribotoxin being secreted through the cytoplasmic membrane of the host after gene expression, characterised in that:

a) the host is protease deficient and/or;

b) degradation of the expressed ribotoxin is suppressed after culture of the procaryotic host by:

i) protease inhibitors and/or;

ii) rapid processing;

iii) processing at chilled temperatures supernatant.

According to another aspect of the present invention there is provided a procaryotic host cell transformed with a vector incorporating a gene for expression of a biologically active ribotoxin able to cleave a single phosphodiester bond of 28S rRNA in a 60S ribosomal subunit, the gene being under control of expression signals compatible with the host and the vector being for directing secretion of the ribotoxin through the cytoplasmic membrane of the host characterised in that the host cell is protease deficient.

Engineering *E. coli* to secrete heterologous gene products has been reviewed by J. A. Stader and T. J. Silhavy in Methods of Enzymology, 185, Academic Press 1990, Edited by D. V. Goeddel.

GLOSSARY OF TERMS

The following glossary is provided in order to assist the reader of the specification:

The term "conventional hosts" refers to hosts having significant protease activity such as hosts in which no measures have been taken to reduce protease activity.

The term "ribotoxins" includes ribotoxins as found in nature or recombinant versions thereof and analogues of such ribotoxins. Fusion proteins, especially biologically active fusion proteins, are also contemplated. Preferably native ribotoxins are restrictocin, mitogillin and alpha-sarcin, more preferably restrictocin and mitogillin and especially restrictocin. Analogues may be derived from native ribotoxins or from other analogues by recombinant DNA techniques such as for example by site directed mutagenesis. Analogues may also be prepared via total gene synthesis from oligonucleotides. Oligonucleotide synthesis has been reviewed by M. J. Gait in Oligonucleotide Synthesis, IRL Press 1984. Total gene synthesis has been described by M. Edwards in International Biotechnology Lab. 5(3) 19-25, 1987.

The term "able to cleave a single phosphodiester bond of 28S rRNA in a 60S ribosomal subunit" as used herein relates to the extremely selective action of the class of ribotoxins typified by restrictocin, mitogillin and alpha-sarcin (Wool, I. G., January 1984, Trends Biochem. Sci. 14-17). Intact eucaryotic ribosomes have a sedimentation coefficient of 80S and are composed of 60S and 40S subunits. The 60S subunit generally contains 28S rRNA (the yeast molecule is smaller) about 4700 nucleotides long. Alpha-sarcin produces a single fragment of 393 nucleotides derived from the 3'end of 28S rRMA and the cleavage produces 3'phosphate and 5'hydroxy groups. The substrate must not be free rRNA since with free 28S rRNA the toxin causes extensive degradation of the nucleic acid. The fragment can also be generated from intact 80S ribosomes but not from the 40S ribosomal subunit. This class of ribotoxins has an extremely selective mode of action and their structure has been highly conserved. Ribotoxin analogues having the extremely selective action of this class of ribotoxins include robotoxin analogues described in European patent application No. 92306509.8 (Publication No. EP 524768). The ability to cleave a single phosphodiester bond of 28S rRNA in a 60S ribosomal subunit may be assayed according to the method of Endo, Y. & Wool, I. G. (1982), J. Biol. Chem. 257, 9054–9060. It will be appreciated that there is some variability in the size of the "28S" rRNA subunit over the spectrum of eucaryotic organisms.

The term "protease deficient" as used herein in relation to strains of microorganism relates to the half life of expressed ribotoxin according generally to the pulse-chase method described in Example 3. For a strain to be protease deficient the half life of restrictocin is generally at least 30 min. In preferred strains restrictocin is essentially undegraded 64 min after expression.

The skilled worker will appreciate that "secretion through the cytoplasmic membrane" refers to the membrane surrounding the cytoplasm of the cell. In Gram negative organisms such as *E. coli* there is another membrane (the outer membrane) surrounding the cytoplasmic membrane; the region between the two membranes defining a periplasm. Secretion of protein through the cytoplasmic membrane in Gram negative organisms generally leads to accumulation of protein in the periplasm, although some leakage of protein through the outer membrane into surrounding medium may also be detected.

The term "processing", when used in the context of 'rapid processing' or 'processing at chilled temperatures', refers to the period during post-culture handling of expressed ribotoxin when proteases from the procaryotic host might significantly degrade the ribotoxin.

The term "rapid", when used in the context of 'rapid processing', refers to the time necessary to prevent very substantial degradation of expressed ribotoxin during processing to the point where yields are unuseable. For example if the time is equal to the relevant half-life of the expressed ribotoxin then about half of the expressed ribotoxin would be degraded, thereby reducing the yield by half. However if expressed ribotoxin was present after culture of the host in sufficient yield then a 50% loss thereof might not be unuseable. Generally the processing is optimally performed as rapidly as practicable in the circumstances. Preferably the rapid processing is completed within 60 min, more preferably the rapid processing is completed within 40 min, more preferably the rapid processing is completed within 30 min, more preferably the rapid processing is completed within 20 min and especially the rapid processing is completed within 10 min.

The term "chilled temperatures", when used in the context of 'processing at chilled temperatures', refers to temperatures necessary to prevent very substantial degradation of expressed ribotoxin during processing to the point where yields are unuseable. The necessary temperatures will depend on the yield of ribotoxin after culture of the host. Generally the processing is optimally performed at temperatures as chilled as is practical in the circumstances but without freezing. Preferred temperatures are just above freezing—15° C., more preferred temperatures are just above freezing—10° C., more preferred temperatures are just above freezing—6° C. and especially preferred temperatures are just above freezing—4° C.

The nucleotide sequences of the top strand of RBS (ribosome binding site) sequences described herein are:
1) for RBS 7, as set out within SEQ. ID. NO.11;
CAATCTAGAG GGTATTAATA ATGTTC-CCAT TGGAGGATGA TTAAATG
2) for RBS 10, as set out within SEQ. ID. NO.13;
CAATAACACA GGAACAGATC TATG
3) for RBS 11, as set out within SEQ. ID. NO.15;
CACTAGTTTA GGAAACAGAC CATG

DETAILED DESCRIPTION

Figure 1:
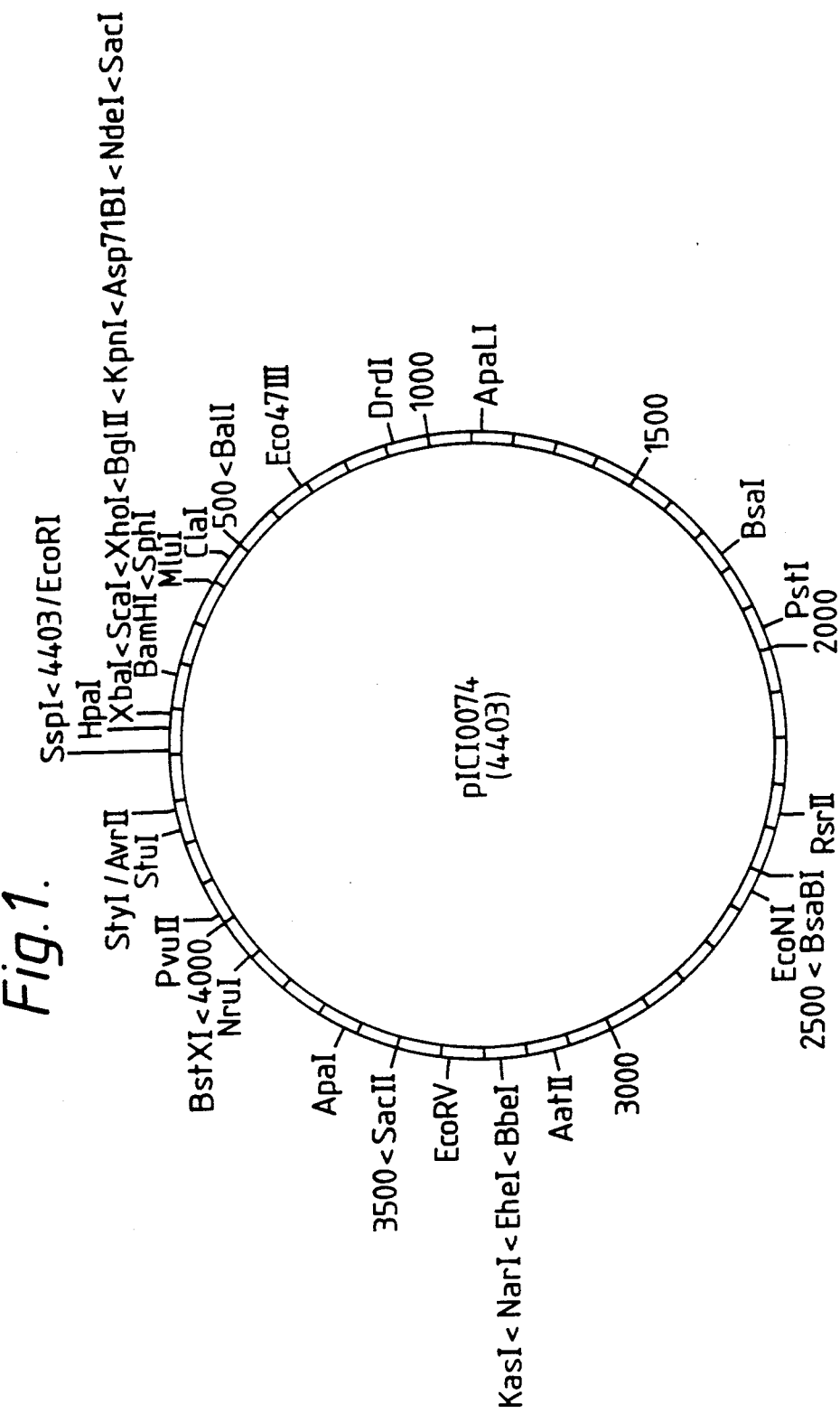
Figure 2:
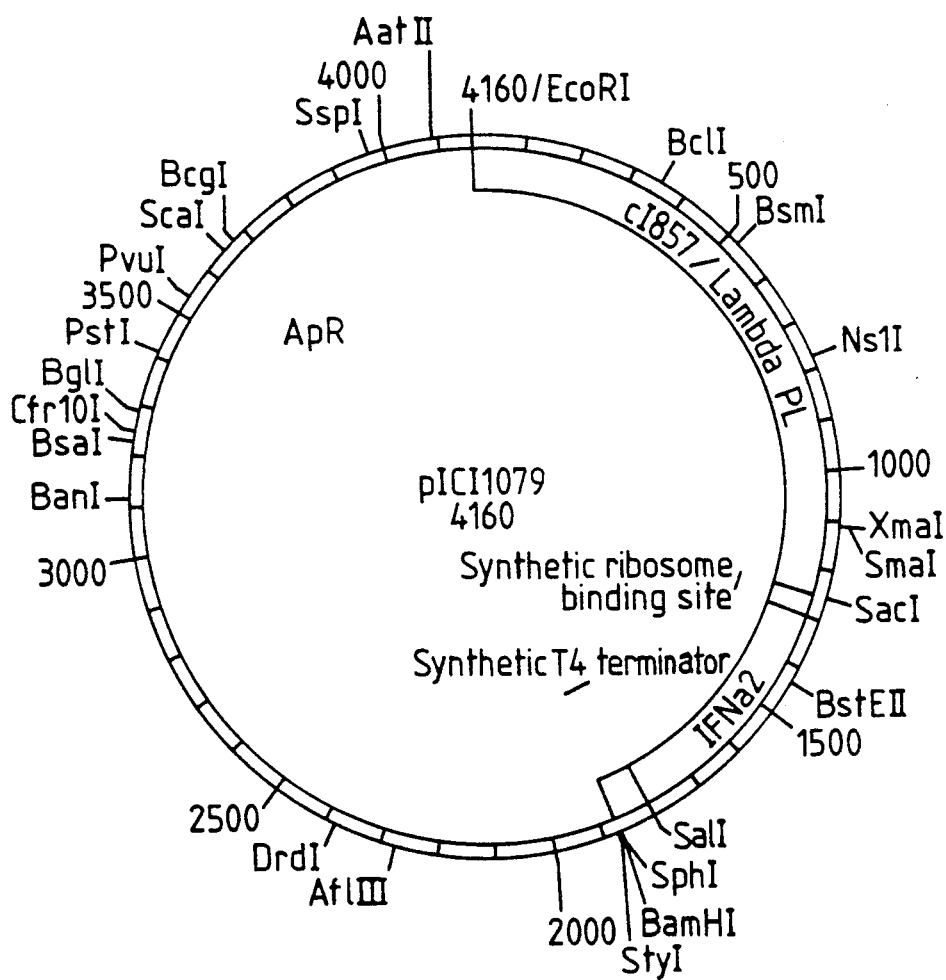
Figure 3A:
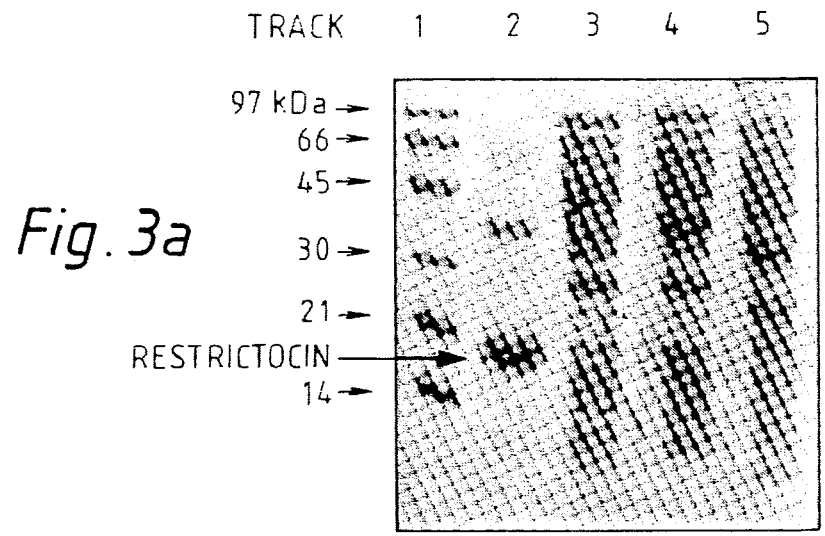
Figure 3B:
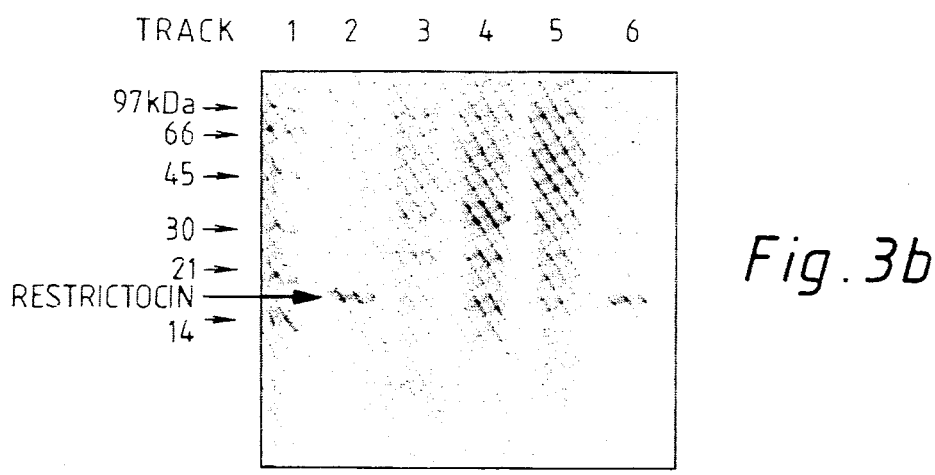

The surprising discovery by the present inventors that a ribotoxin may be accumulated intracellularly in a procaryotic host without causing cell death and the further discovery of the short half life of a ribotoxin in a procaryotic host means that ribotoxin may advantageously be accumulated intracellularly, for example in the cytoplasm of a host cell, if
a) the rate of expression of the ribotoxin intracellularly is enhanced to exceed the rate of proteolysis of the ribotoxin formed;
b) the rate of proteolysis of the ribotoxin formed is reduced such that the rate of expression of ribotoxin intracellularly exceeds the rate of proteolysis of the ribotoxin formed; or
c) the rate of expression of the ribotoxin intracellularly is enhanced and the rate of proteolysis of the ribotoxin formed is reduced such that the rate of expression of ribotoxin intracellularly exceeds the rate of proteolysis of the ribotoxin formed.

Preferably the method of the present invention comprises culture of a protease deficient procaryotic host carrying a vector with a gene for expression of the ribotoxin under control of expression signals compatible with the host. The protease deficient procaryotic host is preferably a bacterium, more preferably *E. coli*, particularly *E. coli* strains deficient in the activity of the protease La, and especially MSD 460 [NCIMB 40469 (see hereinafter)].

Where a protease deficient host is used, the method of the present invention is desirably effected to produce a native ribotoxin having a half life of less than 1 h in conventional hosts (as herein defined), more preferably a half life of less than 30 min in conventional hosts, more preferably a half life of less than 20 min in conventional hosts, more preferably a half life of less than 10 min in conventional hosts and especially a half life of less than 5 min in conventional hosts.

Whilst the use of a protease deficient strain as procaryotic host is preferred it is by no means essential. Thus for example a protease inhibitor such as for example cysteine protease inhibitors such as iodoacetic acid or L-trans-epoxysuccinyl-leucylamide-cysteine (4-guanidino)-butane (E64), cysteine/serine protease inhibitors such as leupeptin and phenyl methylsulphonyl fluoride (PMSF), serine protease inhibitors such as benzamidine and metalloprotease inhibitors such as phenanthroline, ethylenediamine tetraacetic acid (EDTA) and ethylenebis (oxyethylenenitrilo)tetraacetic acid (EGTA) may be used when a non-protease deficient strain of procaryotic host is employed.

Further examples of protease inhibitors are given in "proteolytic enzymes—a practical approach" Edited by R. J. Beynon and J. S. Bond, IRL Press at Oxford University Press.

Where a non-protease deficient strain of procaryotic host is used it is desirable that the half life of the ribotoxin is as long as possible, preferably at least 10 minutes and more preferably at least 15 minutes. Where a non-protease deficient strain is used, recovery of ribotoxin is effected under conditions effective to minimise the rate of degradation of the ribotoxin. The conditions selected for use will depend on the non-protease deficient strain employed, but in general recovery is desirably effected as rapidly as possible, preferably in the presence of a protease inhibitor and advantageously at a temperature of from 0° to 10° C., preferably 0° to 5° C., especially about 0° C. The temperature will normally be selected such that freezing is avoided. In this sense "recovery" is intended to mean that proteolytic factors are substantially removed from contact with the ribotoxin for example by fractionation/purification of ribotoxin away from proteolytic factors present.

The methods of the present invention are preferably effected using a strong promoter and ribosome binding site (RBS) for producing a high rate of expression of ribotoxin such as a λpL inducible promoter.

Further promoters that may conveniently be used include λpR, tac, 1pp and strong coliphage promoters such as promoters from T5 and T7 such as T7A1 and T7A3. Furthermore the trp promoter may also be employed to produce a good rate of expression of ribotoxin. Promoters that may be of interest in the expression of ribotoxins are described in the EMBO Journal, Vol 5, No. 11, pages 2987–2994 (1986) (Promoters of Escherichia coli: a hierarchy of in vivo strength indicates alternate structures) by Ulrich Deuschle et al.

Moreover the ribosome binding site (RBS) may also influence the rate of expression of the ribotoxin and the use of RBS No 7 (as hereinafter defined) has been found to produce a high rate of expression particularly when used together with the λpL promoter.

BRIEF DESCRIPTION OF THE DRAWINGS

FIG. 1 shows a restriction map of pICI0074;

FIG. 2 shows a restriction map of pICI1079;

FIG. 3A and 3B show the result of sodium dodecyl sulphate (SDS) polyacrylamide gel electrophoresis (PAGE) analysis of cell paste from Examples 10 and 11.

FIG. 4 shows the examination by SDS-PAGE of aliquots taken from fractions collected as described in part (vi) of Example 12.

In the drawings FIG. 3A shows the result of SDS-PAGE analysis of cell paste obtained according to Example 10 using a 12.5% Tris-glycine reducing gel. A putative 17 kDa restrictocin band is identified. Track 1 is a molecular weight standard and Track 2 is a restrictocin standard (5 μg). Track 3 is lysate supernatant (10 μl) of 300 ml total. Track 4 is whole lysate (10 μl) and Track 5 is a lysate pellet (5 μl of 200 ml total).

FIG. 3B shows the result of SDS-PAGE analysis of cell paste obtained according to Example 11 using a 12.5% Tris-glycine reducing gel. A putative 17 kDa restrictocin band is identified. Track 1 is a molecular weight standard (2 μg). Track 2 is a restriction standard (5 μg). Track 3 is whole lysate (2 μl). Track 4 is a lysate pellet (5 μl of 2 L total). Track 5 is a lysate supernatant (10 μl) of 7 L total and Track 6 is a restrictocin standard (2 μg).

FIG. 4 shows the results of examining, by SDS-PAGE, fractions collected as described in part (vi) of Example 12. A 12.5% Tris-glycine non-reducing gel is employed and the tracks are as follows:

| Track | |
|---|---|
| 1 | Mol. wt. stds |
| 2 | Restrictocin Standard (2 μg) |
| 3 | Amicon eluate (40 μl) |
| 4 | Mimetic green pool loaded on S-200 (20 μl) |
| 5 | S-200 column fraction 20 (20 μl) |
| 6 | S-200 column fraction 21 |
| 7 | S-200 column fraction 22 |
| 8 | S-200 column fraction 23 |
| 9 | S-200 column fraction 24 |
| 10 | S-200 column fraction 25 |

The following microorganisms and plasmids are referred to in the present specification and the common name, genotype and source are detailed below:

TABLE 1

| MSD No | Common Name(s) | Genotype | Source |
|---|---|---|---|
| 101 | W3110/ CGSC 4474 | Wild type | CGSC 4474 |
| 199 | SG4044 | F⁻Δ(gal-blu) lac lon100 | NCIMB 40468 |
| 200 | MC102/ CGSC 4434 | F⁻leuB thi trPE capR9 lacY galK | CGSC 4434 |
| 262 | K165/ CGSC 6769 | lacZ53(am) phoA5(am) lambda-supC91(ts) trp-48(am) relA1 rpsL150 malT66 (am-lambda R) htpRl(am) spoTl supC47 | CGSC 6769 |
| 460 | W3110lon | W3110 lon100 | NCIMB 40469 |
| 462 | W3110 Δlac | | NCIMB 40370 (see hereinafter) |
| 500 | K165lon | K165 lon100 | NCIMB 40470 |
| 623 | MM294 | F- supE44 lamda- endA thi-1 hsdR17 | CGSC 6315 |
| — | MC1061 | araD139 delta(ara leu)7697 lac74 galU hsdR rpsL | ATCC 53338 |
| — | JM103 | Delta(lac pro) thi rpsL supE andAS sbcB hsdR F' (traD36 proAB lacIqZ) | ATCC 39404 |

Sources designated CGSC may be obtained from the *E. coli* Genetic Stock Centre, Yale University, U.S.A. Sources designated ATCC may be obtained from the American Type Culture Collection, Rockville, U.S.A. The number immediately following the letters CGSC or ATCC represents the relevant accession number of the microorganism. Sources designated NCIMB have been deposited under the Budapest Treaty with the National Collections of Industrial and Marine Bacteria Limited (NCIMB), 23 St Machar Drive, Aberdeen, AB2 1RY, Scotland, United Kingdom and the number quoted is the relevant accession number. The date of deposit of NCIMB 40468, 40469 and 40470 was Jan. 9, 1992.

With regard to the plasmids employed, all may be prepared as described herein from pICI1079 (NCIMB No. 40370, date of deposit Feb. 19, 1991) pICI0074 and pICI0148 (NCIMB No. 40471 date of deposit Jan. 9, 1992). The plasmid pICI1079 has been deposited in MSD462 (see hereinbefore) and thus NCIMB 40370 may be used as a source of pICI1079, *E coli* MSD462 or both such plasmid and microorganism. The production of pICI0074 is described under the codename pLB014 in the European Patent Publication No. 459630A2 published Dec. 4, 1991 and pICI1079 is also described therein.

The invention will now be illustrated but not limited by reference to the following examples.

In the sequence information set out in the present specification the symbols employed are as required by the Rules for Nucleotide and/or Amino Acid Sequence Disclosures of the European, Japanese and U.S. Patent Offices, but for the avoidance of any doubt base codes used are as follows:

| Symbol | Meaning |
| --- | --- |
| A | A; adenine |
| C | C; cytosine |
| G | G; guanine |
| T | T; thymine |
| R | A or G |
| W | A or T |
| S | C or G |
| Y | C or T |
| N | A or C or G or T |

Amino acid three-letter abbreviations are as follows; Ala (Alanine), Arg (Arginine), Asn (Asparagine), Asp Aspartic Acid (Aspartate), Cys (Cystein), Gln (Glutamine), Glu Glutamine Acid (Glutamate), Gly (Glycine), His (Histidine), Ile (Isoleucine), Leu (Leucine), Lys (Lysine), Met (Methionine), Phe (Phenylalanine), Pro (Proline), Ser (Serine), Thr (Threonine), Trp (Tryptophan), Tyr (Tyrosine), Val (Valine) and Xaa (Unknown).

REFERENCE EXAMPLE A

Genomic deoxyribonucleic acid (DNA) was isolated from the fungus *Aspergillus restrictus* as follows. A portion of the DNA containing the coding sequence for mature restrictocin was amplified using the polymerase chain reaction as described by Kleppe et al in J. Mol. Biol., 56, 341-361, (1971), and Saiki et al in Science, 239, 487-491, (1988). The polymerase chain reaction was performed using the thermostable DNA polymerase isolated from the bacterium *Thermus aquaticus* described by Chien et al in Biochemistry, 27, 1550-1557, (1976).

Oligodeoxyribonucleotide (hereinafter referred to as oligonucleotide) primers were designed for the polymerase chain reaction according to the possible DNA coding sequences for restrictocin. This was done using the primary (amino acid sequence) structure of restrictocin reported by Lopez-Otin et al (Eur. J. Biochem. 143, p 621-634). The nucleotide sequences of the oligonucleotide primers were variable at specific positions to allow for the degeneracy of the genetic code. Special features were introduced into the oligonucleotide primer sequences however such that not all possible codons for a given amino acid were present. The rationale being to maximise codon usage to those codons found in highly expressed genes of *E. coli*. A further feature of the design of the oligonucleotide primers was to introduce the ability of the primers to generate analogues of the protein encoded by the DNA sequence bounded by the oligonucleotide primers when used in the polymerase chain reaction. A further feature of oligonucleotide primer design was the introduction of restriction enzyme recognition sequences to facilitate the cloning of polymerase chain reaction products derived from the use of the oligonucleotide primers.

The restrictocin PCR products were initially cloned into a M13 vector to allow sequencing and subsequently to allow analogue generation by site directed mutagenesis. A coding sequence was obtained which was consistent with the published amino acid sequence for mature restrictocin except for a discrepancy at amino acid 115. The published amino acid sequence stated this is an asparagine residue (Lopez-Otin et al (1984), 143, p621-634), but four of our PCR products sequenced indicated there was an aspartic acid residue (GAC) at position 115. The publication of the genomic sequence for restrictocin (Lamy, B. and Davies, J. (1991) Nucleic acids Res. 19(5), p1001-1006) supported our assignment suggesting the originally published amino acid sequence is incorrect. Hence, our restrictocin coding sequence (see sequence ID no. 10) coded for the same protein as predicted for mature restrictocin from the genomic sequence.

The coding sequence was cloned into the ICI expression vector, pICI0122. The derivation of pICI0122 is described below. This vector contains a lambdaPL heat inducible promoter and a ribosome binding site upstream of a polylinker sequence and a T4 transcription termination sequence. Thus pICI0122 corresponds to pICI1079 as hereinbefore described except that pICI0122 contains a $Tet^R$ as opposed to an $Amp^R$ gene and further contains no gene coding for expression of a protein whereas pICI1079 contains the IFNα gene. The restrictocin gene was cloned into the polylinker sequence of pICI0122 such that the first codon of the restrictocin sequence was fused in frame to the initiation codon (ATG) of the expression vector generating lambdaPL-RBS7-RES (pICI1453).

The vector was initially transferred into strain MSD 462. MSD 462 was obtained by deleting the lactose operon from *E. coli* strain W3110 using known methods. Following growth and temperature shock induction, no band corresponding to restrictocin could be detected by one dimensional SDS-PAGE (sodium dodecyl sulphate-polyacrylamide gel electrophoresis). To test if any expression was occurring a 35-S methionine pulse-chase labelling experiment was performed as described below, followed by SDS-PAGE and autoradiography. Cultures were grown at 37° C. to an OD550=0.5 in M9 medium supplemented with 15 μg/ml tetracycline and induced for 1.5 h using a 42° C. temperature shock. M9 medium comprises 6 g/l di-sodium hydrogen orthophosphate, 3 g/l potassium dihydrogen orthophosphate, 0.5 g/l sodium chloride, 1.0 g/l ammonium chloride, 1 mM magnesium sulphate, 0.1 mM calcium chloride, 2 g/l glucose and 4 μg/ml thiamine. 500 ul of culture was then labelled for 90 s with 125 μCi 35S-Methionine and then chased with a 10,000 molar excess of unlabelled methionine. Samples (50 μl) were removed at 0,4,8,32 and 64 mins post labelling and analysed for restrictocin expression/accumulation by SDS-PAGE followed by autoradiography. The labelling and chase were carried out at 42° C.

This demonstrated that restrictocin was indeed being synthesised, but had a remarkably short half life (about 14 min) indicating instability was preventing accumulation of the protein. To overcome this, the vector lambdaPL-RBS7-RES (pICI1453) was transformed into a protease deficient strain of *E. coli* termed MSD 460. Coomassie blue staining analysis of SDS-PAGE gels containing lysates of temperature induced cells detected restrictocin accumulation. MSD460 transformed with lambdaPL-RBS7-RES (pICI1453) gave accumulation of restrictocin at 5% of total cellular protein when grown in shake flasks and about 10% accumulation has been obtained in 20 L fermentations.

Detailed PCR methodology for cloning the restriction sequence and subsequent subcloning of the sequence into a M13 vector and then into expression vectors is set out immediately below.

At all stages of the methodology, except where stated otherwise, standard molecular biological techniques were performed according to Maniatis, T. et al. (1989) Molecular Cloning—A Laboratory Manual, Cold Spring Harbour Press, New York.

*Aspergillus restrictus* was obtained from the American Type Culture Collection (ATCC reference 34475. Spores of the fungus were used to inoculate medium containing 2% w/v soybean meal, 2% w/v corn meal, 1% w/v corn steep liquor, 0.5% w/v calcium carbonate, 1% w/v peptone and 0.5% v/v antifoaming agent comprising 3% w/v octadecanol in lard oil. 50 ml cultures were grown in 250 ml conical flasks, shaken at 30° C. for 48 hours.

Genomic DNA was isolated from *Aspergillus restrictus* as described below. Nine shake flask cultures as above were filtered through a 0.2 micrometer filter. Approximately 5 centimeter cubed portions of the filter retained material were spooned into liquid nitrogen and blended (10 fifteen second pulses) on the "high" setting in liquid nitrogen in a Waring blender. The blended material was transferred to a beaker and the remaining liquid nitrogen allowed to evaporate. 0.3M sodium acetate (150 ml), 20% w/v sodium dodecyl sulphate (15 ml) and phenol/chloroform (15 ml, prepared as described in Maniatis et al, Molecular Cloning; A Laboratory Manual, Cold Spring Harbor Laboratory Press pp.458–459, 1982) was added. The mixture was stirred for 5 minutes. The resulting emulsion was centrifuged at 11000 rpm for 5 minutes. DNA was precipitated from the aqueous phase by addition of ethanol (450 ml) and centrifugation at 11000 rpm for 5 minutes. The pellet was rinsed with 70% v/v ethanol (50 ml), dried in vacuo and resuspended in TE buffer pH8.0 (2 ml, prepared as described in Maniatis et al, Molecular Cloning; A Laboratory Manual, Cold Spring Harbor Laboratory Press p448, 1982) containing ribonuclease A (25 microliters of 100 micrograms per ml in TE as above, heated at 100° C. for 5 minutes). The resulting solution was incubated at 37° C. for 150 minutes then water (7 ml) and 3.0M sodium acetate (1 ml) was added. The DNA was precipitated by the addition of ethanol (30 ml) and centrifugation at 10000 rpm for 1 minute. The pellet was resuspended in 0.3M sodium acetate (10 ml) and extracted with phenol/chloroform (5 ml, as above). The resulting emulsion was centrifuged at 10000 rpm for 5 minutes. DNA was precipitated from the aqueous phase by addition of ethanol (30 ml) and centrifugation at 10000 rpm for 1 minute. The pellet was rinsed with 70% v/v ethanol (40 ml), dried in vacuo and resuspended in TE buffer pH8.0 (5 ml, prepared as described above). This *Aspergillus restrictus* genomic DNA solution was stored at −20° C. when not in use.

Polymerase chain reaction amplification of the *Aspergillus restrictus* genomic DNA was effected by combining 1 microliter of the solution with 100 picomoles oligonucleotide primer SEQ.ID NO. 1, 116 picomoles oligonucleotide primer SEQ ID. NO. 2 and 1.25 units *Thermus aquaticus* DNA polymerase (Cetus "Amplitaq") in a 100 microliter solution that also contained (final concentrations) 100 micromolar each of the four deoxynucleoside triphosphates, dATP, dTTP, dCTP and dGTP, 1.2 mM magnesium chloride, 10 mMTris/HCl pH8.3, 50 mM potassium chloride and 0.01% w/v gelatin. This solution was overlaid with light mineral oil (Sigma) and subjected to thermal cycling. The thermal cycling comprised 10 cycles of 94° C. for 1 minute, 37° C. for 2 minutes and 55° C. for 2 minutes then 20 cycles of 94° C. for 1 minute, 60° C. for 2 minutes and 72° C. for 2 minutes and the final 72° C. incubation was extended to 5 minutes. The main product was isolated after agarose gel electrophoresis, using NA45 paper as recommended by the supplier (Schleicher and Schull). The initial intention was to clone the PCR product into M13mp11 via PvuII and Sal I sites as the oligonucleotides SEQ. ID NOS. 1 and 2 contained these respective recognition sequences. However, sequencing of such M13 clones showed the restrictocin gene to be truncated, which was suspected and later confirmed to be due to a PvuII recognition sequence within the restrictocin gene sequence. Therefore, a second PCR reaction can be performed to introduce other cloning sites into the PCR product, 5' to the restrictocin gene. Approximately 1 microliter of eluate is reamplified, as above, with 100 picomoles each of oligonucleotide primers SEQ ID NOS. 3 and 4. The thermal cycling comprises 5 cycles of 94° C. for 1 minute, 37° C. for 2 minutes and 55° C. for 2 minutes then 25 cycles of 94° C. for 1 minute, 60° C. for 2 minutes and 72° C. for 2 minutes and the final 72° C. incubation is extended to 5 minutes. The main product is isolated after agarose gel electrophoresis, using NA45 paper as recommended by the supplier (Schleicher and Schull).

This purified PCR product is digested with BamHI and SalI and ligated into SalI and BamHI cleaved M13mp11 using T4 DNA ligase according to the supplier's (Boehringer) recommendations. Ligation mixes are used to transfect *E. coli*, strain TG1. TG1 is supplied with the Oligonucleotide-Directed In-Vitro Mutagenesis System Version 2 supplied by Amersham (code RPN-1523). The ligation is performed according to the M13 cloning and sequencing handbook (Amersham). Restrictocin sequences were checked using the dideoxy chain termination approach following instructions supplied with the Sequenase version 2 sequencing kit supplied by United States Biochemicals. Initially M13 and M13 reverse sequencing primers were used (seq ID nos. 5 and 6). The restrictocin sequence was completed using sequencing primers with SEQ ID NOS. 7, 8 and 9. A sequence (SEQ. ID. NO. 10) coding for mature restrictocin was finally obtained. The flanking sequences up to and including the Bam H1 and Sal 1 cloning sites were as follows:

At the 5' end of the restrictocin coding sequence:

```
5'-GGATCCTGCA GCT ACT TGG ACT ...
           Ala Thr Trp Thr
```

At the 3' end of the restrictocin coding sequence:

```
... CTG TGT AGC CAC TAA TAA TAGTCGAC-3'
    Leu Cys Ser His End End End
```

In order to make subsequent subcloning manipulation easier the M13-restrictocin clone was digested with restriction endonucleases SalI and HindIII. The small (approx 0.6 Kb) SalI-HindIII fragment from pBR322 was then cloned into the M13-restrictocin clone backbone. This had the effect of deleting the PstI recognition site adjacent to the SalI site situated 3' of the restrictocin gene.

EXAMPLE 1

This example describes the derivation of *E. coli.* strain MSD460. The lon 100 allele was introduced into MSD 101 (=W3110) by P1 transduction from SG20252 [Trislar and Gottesman (1984) J. Bacteriol. 160, 184–191] and selection for tetracycline resistance followed by screening for sensitivity to nitrofurantoin. [SG20252 has the tetracycline resistance transposon Tn10 closely linked to the lon100 allele. Nitrofurantoin sensitivity is characteristic of lon-strains]. One of the resultant clones was termed MSD310. Presence of the transposon in this strain is undesirable and a derivative lacking this element was isolated by screening for spontaneously arising clones which had lost tetracycline resistance. One of these, termed MSD413 was isolated and shown to retain nitrofurantoin sensitivity. This strain was mucoid, characteristic of Lon-strains. To eliminate this phenotype which is due to overproduction of capsular polysaccharide phage Mu mutagenesis using a derivative of phage Mu termed Mu cts d1 ApR lac was employed. Following infection of MSD413 with Mu cts d1 ApR lac, ampicillin resistant clones were selected on L-amp plates and screened for a non-mucoid phenotype. One such clone termed MSD413*2 was isolated and shown to retain nitrofurantoin sensitivity. We have called the mutation in this strain which suppresses overproduction of capsular polysaccharide som-6. Presence of Mu cts d1 ApR lac in this strain is undesirable. A derivative which has lost the defective phage, but has retained som-6 was isolated by conventional heat curing and screening for loss of ampicillin resistance. One such clone, which appeared to retain som-6 and which was nitrofurantoin sensitive was termed MSD460.

On more extensive characterization, MSD460 was found to require methionine, but not histidine for growth (i.e. was Met-) and was unable to grow on arabinose as sole source of carbon although it retained the ability to grow on glycerol. The most likely interpretation of these data is that MSD460 carries a deletion extending through metG and araFG at minute 45 of the *E. coli* genetic map, but which does not extend beyond the his operon at minute 44 and the glp operon at minute 48.5.

EXAMPLE 2

This example describes direct expression of mature restrictocin. Four restrictocin expression vectors, three containing the lambdaPL promoter with the CI857 temperature sensitive repressor gene, but with different ribosome binding sites, and a further vector containing the Trp promoter, have been assessed in detail.

The generation of expression vectors containing the lambdaPL promoter can all be initiated with the same precursor plasmids, pICI0074 and pICI1079 (MSD462). Vector pICI1079 has been deposited under the Budapest Treaty at the National Collections of Industrial and Marine Bacteria Limited (NCIMB), 23 St. Machar Drive, Aberdeen, AB2 1RY, Scotland, U.K. (NCIMB No. 40370), date of deposit Feb. 19, 1991).

pICI0074 and pICI1079 are digested with EcoRI and SacI. The fragments are then put into a ligation reaction, and the ligation reaction used for transformation of *E. coli.* Screening by restriction mapping is used to identify the recombinant plasmid in which the lambdaPL/CI857 repressor fragment from pICI1079 is inserted into the pICI0074 backbone fragment which contains the tetracycline genes, a cer stability function, multiple restriction cloning sites and the T4 transcription terminator.

In an analogous manner, the initial step in generation of Trp promoter expression vectors is to derive an EcoRI-SacI fragment containing the Trp promoter from the vector, pICI0148. pICI0148 is a pAT153 derivative in which a trp promoter (on a EcoRI-SacI fragment) followed by a partial synthetic interferon gene sequence are inserted into the EcoRI and SalI sites of pAT153. The sequence of this EcoRI-SalI fragment is SEQ. ID. NO. 17:

```
AATTCTGGCA AATATTCTGA AATGAGCTGT TGACAATTAA TCATCGAACT AGTTAACTAG
TACGCAGAGC TCACCAGCAA CTGAACGATC TAAAGCCTGC GTCATCCAGG GTGTTGGCGT
AACCGAAACT CCGCTGATGA AAGAAGACTC CATCCTGGCT GTTCGCAAAT ACTTCCAGCG
TATCACCCTG TACCTGAAAG AGAAGAAATA CAGCCCGTGC GCTTGGGAAG TTGTACGCGC
TGAAATCATG AGATCTTTCA GCCTGTCCAC TAACCTGCAA GAATCTCTGC GTAGCAAAGA
ATAAG
```

The EcoRI and SalI overhangs define the 5' and 3' ends of the sequence respectively. The SacI restriction site is underlined. The Trp promoter fragment is then subcloned into the EcoRI-SacI backbone fragment of pICI1079.

The assembly of the expression vectors is completed by cloning of linker sequences containing different ribosome binding site sequences between the SacI and KpnI sites (i.e. into the polylinker) of the above generated intermediate vectors containing either the lambdaPL or Trp promoter.

The RBS containing linker for generation of expression vector lambdaPL-RBS7 (pICI0122) is made through hybridisation of the two 5' phosphorylated oligonucleotides, SEQ. ID. NOS. 11 and 12:

```
     CAATCTAGAG GGTATTAATA ATGTTCCCAT TGGAGGATGA TTAAATGGTA C
TCGA GTTAGATCTC CCATAATTAT TACAAGGGTA ACCTCCTACT AATTTAC
```

The RBS containing linker for generation of vectors lambdaPL-RBS10 (pICI0123) and Trp-RBS10 (pICI0119) is made through hybridisation of the two 5' phosphorylated oligonucleotides, SEQ. ID. NOS. 13 and 14:

```
CAATAACACA GGAACAGATC TATGGTAC
```

-continued

TCGA GTTATTGTGT CCTTGTCTAG ATAC

The RBS containing linker for generation of lambdaPL-RBS11 (pICI0124) is made through hybridisation of the two 5' phosphorylated oligonucleotides, SEQ. ID. NOS. 15 and 16:

CACTAGTTTA GGAAACAGAC CATGGTAC

TCGA GTGATCAAAT CCTTTGTCTG GTAC

The restrictocin coding sequence (SEQ. ID. No. 10) was cloned into the four expression vectors described above using the subcloning strategy now detailed to generate the following four restrictocin expression vectors:
1) lambdaPL-RBS7-RES (pICI 1453)
2) lambdaPL-RBS10-RES (pICI 1451)
3) TRP-RBS10-RES (pICI 1450)
4) lambdaPL-RBS11-RES (pICI 1462)

Initially the expression vectors were digested with KpnI and then the overhang blunt-ended using T4 DNA polymerase. Then the vectors were further digested with XhoI (like KpnI, situated in the polylinker). Finally the vectors were treated with calf intestinal alkaline phosphatase to prevent subsequent religation of the fragments. The M13-restrictocin clone as digested with PstI and then the overhangs were blunt-ended with T4 DNA polymerase. This was followed by SalI digestion to release the restrictocin coding sequence. A ligation reaction was then performed to insert the restrictocin fragment into the expression vectors. At the 5' end of the restrictocin sequence the ligation is blunt-ended, but the SalI overhang at the 3' end is compatible with the XhoI site. No purification of DNA fragments was necessary because recombinants containing the M13 backbone cannot produce colonies on Ampicillin plate selection following transformation. The PstI/-blunt ending reaction results in the 5' most base of the restrictocin fragment being the first base of the first codon of the restrictocin coding sequence. The KpnI/-blunt ending reaction results in the 3' end of the expression vector backbone reading ATG which is the initiation codon corresponding to the RBS sequence directly upstream. Hence the ligations result in fusion of the restrictocin coding sequence in frame with the translation initiation codon.

Following characterisation, the series of restrictocin expression vectors was transformed into host strain *E. coli* MSD 462. Transformants containing the trp promoter vectors were grown as follows. 10 ml of L-broth+tetracycline (15 μg/ml) was inoculated with a single colony from a fresh plate and grown overnight at 37° C. with gentle shaking. 750 μl of the overnight culture was taken and centrifuged in a microfuge at 6500 rpm for 1 minute. The supernatant was removed and the pellet resuspended in 300 μl of M9 medium supplemented with 0.02% casein acid hydrolysate (Oxoid L41) and 15 μg/ml tetracycline. This was then transferred to a further 10 ml of the above described supplemented M9 medium. This culture was grown for 7 hours or overnight at 37° C. with gentle shaking.

Transformants containing the lambda PL promoter were grown as follows. 75 ml of the supplemented M9 medium (described above) was inoculated with a single colony from a fresh plate and grown overnight at 35° C. with gentle shaking. The $OD_{550}$ was measured and the culture diluted with the same medium to give a 75 ml volume with $OD_{550}=0.1$. This culture was grown at 37° C. with gentle shaking until $OD_{550}=0.4$–0.6 (approx 3–4 hrs.). The incubator temperature was increased to 42° C. and growth continued for a further 3 hours, to allow induction.

Restrictocin accumulation was assessed by Coomassie blue stained SDS-PAGE gels of whole cell lysates of the sampled bacteria according to known methods. Restrictocin accumulation was not detected. In order to determine whether the vectors were expressing restrictocin, a more sensitive 35-S methionine pulse chase labelling experiment was used as set out in detail in Example 3. This unexpectedly demonstrated that restrictocin expression was indeed taking place, but surprisingly, the protein had a short half life in the conventional *E.coli* host strain, MSD462. The half life was only about 14 minutes. Thus the conditions under which samples containing restrictocin are processed may be an important factor in its recovery. In order to overcome this stability problem the vectors were introduced into the protease deficient strain MSD460. Restrictocin production was tested as follows: A single colony isolate was transferred from an overnight tetracycline plate to 75 ml M9 supplemented as above and with 20 mg/L methionine and incubated for 16 h at 37° C. in an orbital shaker. Fresh medium was inoculated as described to OD550=0.1 with O/N culture and incubated at 37° C. with shaking. Growth was monitored until OD550=0.5 and then the shake flask was either transferred to a second orbital shaker pre-warmed to 42° C. and incubated with shaking for 2–4 h (lambda PL vector) or 20 μg/ml indole acrylate was added (trp vector) and the incubation continued for 2–4 h at 37° C. Restrictocin accumulation was determined by SDS-PAGE.

The use of MSD460 had a significant effect on the accumulation level. For example using MSD460 transformed with vector containing the lambda PL promoter and ribosome binding site 7 (lambdaPL-RBS7-RES), restrictocin accumulation levels of 5–10% total cell protein have been obtained.

Other promoter systems are potentially of interest in restrictocin expression, for example the T7A3 promoter with *E.coli.*

EXAMPLE 3

This example describes the determination of the half life of restrictocin in various strains of *E.coli. E.coli.* strains MSD101, 460 and 500 were transformed with plasmid pICI1453 (lambda pL vector) and strain MSD460 transformed with plasmid pICI1450 (trp vector). The resultant strains MSD101 (pICI1453), MSD460 (pICI1453), MSD500 (pICI1453) and MSD 460 (pICI 1450) were purified and maintained in glycerol stocks at −80° C. An aliquot of each culture was removed from stock and streaked onto agar plates of L-tetracycline to give separate single colonies after overnight growth at 37° C. (30° C. for MSD 500 (pICI1453)). A single colony of each culture was removed and inoculated into a 250 ml Erlenmeyer flask containing 75 ml of M9 medium (described hereinafter in Table 2) supplemented with 0.02% w/v casein hydrolysate (Oxoid L.41) and 10 μg/ml tetracycline. The medium was also supplemented with 45 $mgl^{-1}$ methionine (strains MSD460 (pICI1453), MSD460 (pICI1450)) and 20 $mgl^{-1}$ tryptophan (strain MSD500 (pICI1453)). After growth for 16 hours at 37° C. (30° C. for MSD 500

(pICI1453)) on a reciprocating shaker the cultures were harvested, washed twice and resuspended in cold phosphate buffered saline solution (10 mM sodium phosphate, 150 mM sodium chloride, pH 7.4). These cultures were then used to inoculate (to $OD_{550}=0.1$) fresh M9 medium supplemented as described previously but excluding the casein hydrolysate and grown at 37° C. (30° C. for strain MSD 500 pICI1453) on a reciprocating shaker. Growth was monitored until $OD_{550}=0.3-0.5$ when the flasks were either transferred to a second reciprocating shaker pre-warmed to 42° C. and incubated with shaking for a further 1.5 h (lambda pL vector) or 20 µg/ml indole acrylate was added (trp vector) and the incubation continued for 1.5 h at 37° C. 500 µl of induced culture was then labelled for 90 seconds with 125 µCi $^{35}$S-methionine (strains MSD101 (pICI1453), MSD500 (pICI1453)) or with 125 µCi $^{35}$S-cysteine (MSD 460 (pICI 1450), MSD460 (pICI1453) and then chased with a 10,000 molar excess of unlabelled methionine/cysteine as appropriate. Samples (50 µl) were removed at 0, 4, 8, 16, 32 and 64 minutes post labelling and analysed for restrictocin expression/degradation/accumulation by SDS-PAGE followed by laser densitometry scanning of autoradiographs. The labelling and chase were carried out at 42° C. (lambda pL vector) or 37° C. (trp vector). The results are summarized below (Table 3).

TABLE 2

| Composition of M9 medium | |
| --- | --- |
| di-sodium hydrogen orthophosphate | 6 gl$^{-1}$ |
| potassium di-hydrogen orthophosphate | 3 gl$^{-1}$ |
| sodium chloride | 0.5 gl$^{-1}$ |
| ammonium chloride | 1.0 gl$^{-1}$ |
| magnesium sulphate | 1 mM |
| calcium chloride | 0.1 mM |
| glucose | 2 gl$^{-1}$ |
| thiamine | 4 µg/ml |

TABLE 3

| HOST STRAIN | PLASMID | EXPRESSION POST 90s LABEL* | MEASURED HALF LIFE RESTRICTOCIN (t$_{\frac{1}{2}}$) min |
| --- | --- | --- | --- |
| MSD460 | pICI1453 | 13 | STABLE |
| MSD500 | pICI1453 | 11 | STABLE |
| MSD460 | pICI1450 | 26 | STABLE |
| MSD101 | pICI1453 | 12 | 14 (Control) |

*% TMP: as determined by laser densitometry scanning of autoradiographs.

The Example shows the expression obtained and the half life determined (pulse chase method) in respect of restrictocin obtained using a variety of plasmids in a variety of protease deficient strains of *E. coli* compared with a control (protease normal) strain.

EXAMPLE 4

This example describes the influence of promoter and ribosome binding site on restrictocin accumulation. *E. coli* strain MSD460 was transformed with plasmids pICI1453 (lambda pL vector, ribosome binding site (RBS)7), pICI1451 (lambda pL, RBS 10), pICI1462 (lambda pL, RBS11) and pICI1450 (trp vector, RBS 10). The resultant strains were purified and maintained in glycerol stocks at −80° C. Aliquots of each culture including host MSD460 were removed from stock and streaked onto agar plates of L-tetracycline (L-agar for MSD460 host) to give separate single colonies after overnight growth at 37° C. A single colony of each culture was removed and inoculated into a 250 ml Erlenmeyer flask containing 75 ml of M9 medium (described previously) supplemented with 45 $mgl^{-1}$ methionine, 10 μg/ml tetracycline and 0.02% w/v case in hydrolysate (Oxoid L.41) and grown at 37° C. for 16 h on a reciprocating shaker (the tetracycline was omitted for MSD460 host). These flasks were then used to inoculate fresh M9 medium (supplemented as described) to $OD_{550}=0.1$. These cultures were grown at 37° C. on a reciprocating shaker to an $OD_{550}=0.5$. Flasks containing the lambda pL vectors and the untransformed host strain MSD460 were transferred to a second reciprocating shaker pre-warmed to 42° C. and incubated with shaking for 2 h (4 h for host MSD460) or 20 μg/ml indole acrylate was added (trp vector) and the incubation continued for 2 h at 37° C. Restrictocin accumulation was determined by scanning Coomassie stained gels following SDS-PAGE of the sampled bacteria. The results are summarized below in Table 4.

TABLE 4

| STRAIN | PROMOTER | RIBOSOME BINDING SITE | RESTRICTOCIN ACCUMULATION (% TMP)* |
|---|---|---|---|
| MSD460 pICI1453 | lambda pL | 7 | 8 |
| MSD460 pICI1451 | lambda pL | 10 | 2 |
| MSD460 pICI1462 | lambda pL | 11 | 3 |
| MSD460 pICI1450 | trp | 10 | 8 |
| MSD460 | HOST BLANK | — | <1 |

*% TMP (total microbial protein).

This Example shows that the expression may be effected using different promoters and different ribosome binding sites and further that the selection of ribosome binding site and promoter may beneficially affect the accumulation of ribotoxin.

EXAMPLE 5

This example demonstrates the accumulation of restrictocin in various strains of *E. coli*. Protease deficient *E. coli* strains 199, 200, 262, 460 and 500 were transformed with plasmid pICI1453 as described previously. Aliquots of each culture from stock were removed and streaked onto agar plates of L-tetracycline to separate single colonies after overnight growth at the temperature indicated in Table 5. A single colony of each culture was removed and inoculated into a 250 ml Erlenmeyer flask containing 75 ml of M9 medium (described previously) supplemented with 10 μg/ml tetracycline, 0.02% w/v casein hydrolysate and amino acids as indicated in Table 5. Cultures were grown to $OD_{550}=0.5$ as described previously and induced by transferring the flasks to a second incubator pre-warmed to 42° C. After thermal induction for 2 h restrictocin accumulation was determined as described previously by SDS-PAGE. The results are presented in Table 6.

TABLE 5

| Growth temperatures and medium supplements | | |
|---|---|---|
| HOST STRAIN | M9 SUPPLEMENT | *GROWTH TEMPERATURE (°C.) |
| MSD199 | — | 37 |
| MSD200 | 20 $mgl^{-1}$ leucine, 20 $mgl^{-1}$ tryptophan, 68 $mgl^{-1}$ adenine | 37 |
| MSD262 | — | 30 |
| MSD460 | 45 $mgl^{-1}$ methionine | 37 |

TABLE 5-continued

Growth temperatures and medium supplements

| HOST STRAIN | M9 SUPPLEMENT | *GROWTH TEMPERATURE (°C.) |
|---|---|---|
| MSD500 | 20 mgl$^{-1}$ tryptophan | 30 |

*prior to thermal induction (42° C.)

TABLE 6

| HOST STRAIN | ACCM % TMP POST INDUCTION |
|---|---|
| 199 | 8 |
| 200 | 8 |
| 262 | 9 |
| 460 | 8 |
| 500 | 8 |

This Example demonstrates that the accumulation of restrictocin may be effected intracellularly using a wide range of different protease deficient strains of *E. coli*.

EXAMPLE 6

This example compares restrictocin accumulation in an non-protease deficient *E. coli*. strain using cell lysis under chilled conditions in the presence or absence of protease inhibitors. An aliquot of *E. coli.* strain MSD101 (pICI1453) from glycerol stocks at −80° C. was streaked onto an agar plate of L-tetracycline to separate single colonies after overnight growth at 37° C. A single colony of the culture was removed and quickly resuspended in 500 μl of phosphate buffered saline (described previously) 100 μl of this suspension was inoculated into each of two 250 ml Erlenmeyer flasks containing 75 ml of M9 medium (table 1) supplemented with 10 μg/ml tetracycline and 0.02% w/v casein hydrolysate (Oxoid L.41). After growth at 37° C. for 16 h on a reciprocating shaker the contents of the flasks were pooled and used to inoculate to $OD_{550}=0.1$ twenty 250 ml Erlenmeyer flasks containing M9 medium supplemented as described above. The flasks were then grown to $OD_{550}=0.5$ and transferred quickly to a second incubator pre-warmed to 42° C. and the incubation continued at this temperature with shaking for 2 h.

The contents of the flasks were pooled and divided equally into two chilled 1 liter centrifuge bottles (A and B) and the bacteria sampled as described previously to determine restrictocin accumulation. The contents of the centrifuge bottles were then chilled to 4° C. in a dry ice/ethanol mixture and the bacteria harvested in a pre-chilled (4° C.) centrifuge (Sorvall RC-3B) at 7000x g for 30 minutes. The cell pellets were then resuspended in 20 ml cold lysis buffer (as defined below) and transferred to 50 ml plastic centrifuge tubes. 1 mM phenyl methyl sulphonyl fluoride (PMSF), 1 mM EDTA, 1 mM benzamidine and 1 mM iodoacetamide were added to cell resuspension (A). Lysozyme (1 mg/ml) was added then to both suspensions and the incubation continued on ice for 30 minutes prior to the addition of 100 μl DNAase solution (as defined below). The cell resuspensions were incubated on ice for a further 30 minutes. The samples were then sonicated with a 45 second burst at maximum amplitude followed by a 45 second period on ice during which a further 1 mM PMSF was added to cell resuspension (A). The sonication was continued with a further 3×45 second bursts as described above followed by another period on ice for 15 minutes prior to the completion of the lysis with a final 2×45 second bursts. Samples to determine restrictocin accumulation were taken immediately after thermal induction and from cell suspensions A (lysis carried out chilled in the presence of protease inhibitors) and B (lysis carried out chilled but in the absence of protease inhibitors) at various points in the lysis protocol described. The results are presented in table 7.

TABLE 7

| SAMPLE DESCRIPTION | RESTRICTOCIN ACCUMULATION % TMP (A) | (B) |
|---|---|---|
| Post thermal induction | 9 | 9 |
| Post harvest and resuspension | 9 | 7 |
| Prior to sonication | 5 | 9 |
| Post sonication | 7 | 6 |

Lysis Buffer is 30% Sucrose (375 ml); 1M Tris-HCl [Tris (Hydroxymethyl) aminomethane hydrochloride] (37.5 ml); 0.2M EDTA pH 8.0 (187.5 ml); made up to 750 ml with deionized water (final pH 8.0). DNAase Solution is 1M Tris-HCl (37.5 ml); 1M $MgCl_2$ (70.0 ml); 1M $CaCl_2$ (1.0 ml); made up to 250 ml with deionized water (final pH 7.5) and 1 mg/ml DNAase added.

This Example demonstrates that the use of a protease deficient strain, whilst preferable, is not essential.

EXAMPLE 7

This example demonstrates the effect of processing temperature on restrictocin accumulation. *E. coli* strain MSD623 was transformed with plasmid pICI1453 and the resultant strain MSD623 pICI1453 purified and maintained in glycerol stocks at −80° C. An aliquot of MSD623 pICI1453 was removed from stock and streaked onto an agar plate of L-tetracycline to separate single colonies after overnight growth at 37° C. A single colony of the culture was removed and resuspended in 500 μl of phosphate buffered saline (described previously). 100 μl of the suspension was inoculated into two 250 ml Erlenmeyer flasks containing 75 ml of M9 medium (table 1) supplemented with 10 μg/ml tetracycline and 0.02% w/v casein hydrolysate (Oxoid L.41). After growth at 37° C. for 16 h on a reciprocating shaker the contents of the flasks were pooled and used to inoculate to $OD_{550}=0.1$ six 250 ml Erlenmeyer flasks containing M9 medium supplemented as described as above. The flasks were then grown to $OD_{550}=0.5$ and transferred to a second incubator pre-warmed to 42° C. and the incubation continued at this temperature with shaking for 2 h. The contents of the flasks were then transferred to a 1 liter centrifuge bottle pre-cooled to 4° C. The culture was cooled to 4° C. in a dry ice/ethanol mixture and the cells harvested in a centrifuge (Sorvall RC-3B, 4° C.) at 7000x g for 30 minutes. The cell pellet was then resuspended in 25 ml of lysis buffer (4° C., table 2 as described below in Example 9) and transferred to a 50 ml plastic centrifuge tube. Lysozyme (1 mg/ml) was then added to the cell suspension and the incubation continued on ice for a period of 30 minutes prior to the addition of 100 ul of DNAase solution (table 3 as described below in Example 9). The suspension was maintained on ice for a further 30 minutes and sonicated with six 45 second bursts at maximum amplitude each followed by a 45 second "rest" on ice after which microscopic examination indicated that >95% of the cells had been lysed. Samples to determine restrictocin accumulation were taken immediately after thermal induction and from the cell suspensions at various points in the lysis protocol.

The protocol was repeated exactly as described above but following thermal induction of the culture the cells were maintained at 10° C. and at 20° C. during harvesting and subsequent processing.

The lysis protocols at 4°, 10° and 20° C. described above were repeated using E. coli. strain MSD101 (pICI 1453).

The influence of harvest and processing temperature on restrictocin accumulation is presented in table 8.

tents of the flasks were pooled and the bacteria sampled as described previously to determine restrictocin accumulation. The contents of the centrifuge bottle were then chilled to 4° C. in a dry ice/ethanol mixture and the bacteria harvested in a pre-chilled (4° C.) centrifuge (Sorvall RC-3B) at 7000x g for 30 minutes. The cell pellet was then resuspended in 25 ml lysis buffer (as described below) at 10° C. (as described below) and transferred to a 50 ml plastic centrifuge tube. 1 mM phenyl sulphonyl fluoride (PMSF), 1 mM EDTA, 1 mM benzamidine and 1 mM iodoacetamide were then

TABLE 8

| Strain | Processing Temperature °C. | Restrictocin accumulation % TMP[3,4] | | | | |
|---|---|---|---|---|---|---|
| | | Post Induction | Post Harvest | Post Lysozyme Incubation | Post DNAase Incubation | Post Sonication |
| MSD101 | 4 | 7 | 7 | 9 | 8 | 8 |
| pICI1453 | 10 | 6 | 4 | 2 | LOW[1] | LOW[1] |
| | 20 | 6 | 3 | 2 | LOW[1] | LOW[1] |
| MSD623 | 4 | 5 | 4 | 4 | 4 | 3 |
| pICI1453 | 10 | 6 | 1 | 2 | LOW[1] | LOW[1] |
| | 20 | 6 | 2 | 1 | LOW[1] | LOW[1] |
| Time Post Induction (minutes) | — | 0 | 35[2] | 65 | 95 | 104 |

[1]Accumulation levels below detection limit of laser densitometry scanning of Coomassie blue stained SDS-PAGE (<1% TMP)
[2]Time is total time including acceleration and decleration times.
[3]TMP = Total Microbial Protein
[4]Values corrected for the presence of lysozyme in samples post harvest.

EXAMPLE 8

This example demonstrates the effect of processing time on restrictocin recovery. The growth, induction, harvest and processing protocols (10° C. and 20° C.) described in Example 7 were repeated using strains MSD101 pICI1453 and MSD623 pICI1453 with the following reductions in the processing time:
(i) Induced cells were harvested at 7000x g for 10 minutes (total time 15 minutes as (2) above).
(ii) The incubation times with lysozyme and DNAase were reduced to 5 minutes respectively.

The cell suspensions were sonicated as described in example 1. Microscopic examination of the suspensions post sonication indicated that >95% of the cells had been lysed.

The influence of processing time on restrictocin accumulation level is presented in table 9 below.

added to the cell suspension followed by lysozyme (1 mg/ml) and the incubation continued at 10° C. for 30 minutes prior to the addition of 100 μl DNAase solution (as described below) and 1 mM PMSF. The cell suspension was incubated (10° C.) for a further 30 minutes and 1 mM PMSF added. The sample was then sonicated with 3×45 second bursts at maximum amplitude each followed by a 45 second "rest" at 10° C. A further 1 mM PMSF was added and the sonication was continued with a further 3×45 second bursts as described above. Microscpic examination indicated that >95% of the cells had been lysed. Samples to determine restrictocin accumulation were taken immediately after thermal induction and during the processing as described previously.

The protocol described above was repeated using strain MSD101 pICI1453 except that the process was maintained at 20° C. instead of 10° C.

TABLE 9

| Strain | Processing Temperature °C. | Restrictocin accumulation % TMP[3,4] | | | | |
|---|---|---|---|---|---|---|
| | | Post Induction | Post Harvest | Post Lysozyme Incubation | Post DNAase Incubation | Post Sonication |
| MSD101 | 10 | 5 | 4 | 5 | 4 | 4 |
| pICI1453 | 20 | 5 | 2 | LOW[1] | LOV(1) | LOW[1] |
| MSD623 | 10 | 5 | 5 | 1 | LOW[1] | LOW[1] |
| pICI1453 | 20 | 5 | 1 | LOW[1] | LOW[1] | LOW(1) |
| Time Post Induction (minutes) | — | 0 | 15[2] | 20 | 25 | 34 |

[1]-[4]As described for Table 8.

EXAMPLE 9

This example describes the effect of protease inhibitors on restrictocin accumulation during processing at 10° C. and 20° C. Strain MSD101 pICI1453 was grown and induced as described above in example 6. The con- The process described above was repeated (10° and 20° C.) using strain MSD623 pICI1453.

The infuence of the addition of protease inhibitors on restrictocin accumulation levels during processing at 10° and 20° C. is presented in table 10.

TABLE 10

| Strain | Processing Temperature °C. | Restrictocin accumulation % TMP[(3,4)] | | | |
|---|---|---|---|---|---|
| | | Post Induction | Post Harvest | Post Lysozyme Incubation | Post DNAase Incubation | Post Sonication |
| MSD101 | 10 | 8 | 7 | 7 | 9 | 8 |
| pICI1453 | 20 | 8 | 8 | 8 | 6 | 6 |
| MSD623 | 10 | 4 | 5 | 5 | 4 | 4 |
| pICI1453 | 20 | 4 | 3 | 4 | 4 | 4 |
| Time Post Induction | — | 0 | 35[(2)] | 65 | 95 | 104 |

[(2)-(4)]As described above in Table 8.

Lysis Buffer is: 30% Sucrose (375 ml); 1M Tris - HCl (37.5 ml); 0.4M EDTA pH8.0 (187.5 ml); made up to 750 ml with deionized water (final pH 8.0).

DNAase Solution is: 1M Tris-HCl (37.5 ml); 1M $MgCl_2$ (70.0 ml); 1M $CaCl_2$ (1.0 ml); made up to 250 ml with deionized water (final pH 7.5); 1 mg/ml DNAase.

EXAMPLE 10

This example describes preparation of cell paste containing restrictocin. E. coli strain MSD460 pICI1453 (described previously) from glycerol stocks at −80° C. was streaked onto agar plates of L-tetracycline to separate single colonies after overnight growth at 37° C. A single colony of MSD460 pICI1453 was removed and resuspended in a 10 ml L-tetracycline broth and 100 μl immediately inoculated into each of ten 250 ml Erlenmeyer flasks containing 75 ml of L-tetracycline broth. After growth for 16 h at 37° C. on a reciprocating shaker the contents of the flasks were pooled and used to inoculate a single fermenter containing the growth medium described in Table 11. The fermentation was carried out at a temperature of 37° C. and pH, controlled by automatic addition of 6M sodium hydroxide solution, of pH 6.7. The dissolved oxygen tension (dOT) set-point was 50% air saturation and was controlled by automatic adjustment of the fermenter stirrer speed. Air flow to the fermenter was 20 L/min corresponding to 1 volume volume per minute (VVM). A solution of yeast extract was fed into the fermenter at a rate of 1.7 g/L/h from 4.5 h post inoculation. When the culture $OD_{550}$ reached 15, the fermentation temperature was increased to 42° C. and the fermentation continued at this temperature under the conditions described above for a further 7 h at which point the biomass concentration was 11 g/l (dry weight) and restriction accumulation was 8% of total microbial protein. The bacteria were harvested in 1 L centrifuge bottles in a Sorvall RC-3B centrifuge (7000x g, 4° C., 30 min) and the cell paste stored frozen at −80° C. prior to processing as described in Example 12.

EXAMPLE 11

This example describes preparation of cell paste containing restrictocin. The fermentation process described in Example 10 was repeated as described with the following modifications.

(i) The air flow to the fermenter was increased to 2.5 VVM when the fermenter stirrer speed reached approximately 80–90% of its maximum.

(ii) When the culture $OD_{550}$ reached 50 the yeast extract feed rate was increased to 3.4 g/L/h.

(iii) The culture was induced by raising the fermentation temperature from 37° C. to 42° C. when the culture reached an $OD_{550}=80$. The fermentation was maintained at 42° C. for 5 h at which point the biomass concentration was 33 g/l (dry weight) and restrictocin accumulation was 10% of total microbial protein. The bacteria were harvested as described in Example 10 and subsequently processed as described in Example 12.

(iv) A feed containing glycerol (714 g/L) and ammonium sulphate (143 g/L) was fed into the fermenter as described below.

Between 7–8 h post fermenter inoculation the supply of carbon source (glycerol) in the fermentation became exhausted leading to a rapid rise in dOT from 50% air saturation. At this point, the feed described above was pumped into the fermenter at a rate which restricted the bacterial oxygen uptake rate (OUR) to approximately 80% of the fermenters maximum oxygen transfer rate (OTR) (under the conditions described) whilst first returning and then maintaining the dOT at 50% air saturation.

TABLE 11

| Growth medium | g/L (deionized water) |
|---|---|
| Potassium dihydrogen orthophosphate | 3.0 |
| di-Sodium hydrogen orthophosphate | 6.0 |
| Sodium chloride | 0.5 |
| Casein hydrolysate (Oxoid L.41) | 2.0 |
| Ammonium sulphate | 10.0 |
| Glycerol | 35.0 |
| Yeast extract (Difco) | 20.0 |
| Magnesium sulphate 7-hydrate | 0.5 |
| Calcium chloride 2-hydrate | 0.03 |
| Thiamine | 0.008 |
| Iron sulphate 7-hydrate/Citric acid | 0.04/0.02 |
| Trace element solution (TES)* | (0.5 ml/L) |
| Tetracycline | (10 mg/L) mg/10 ml |
| *Trace element solution | (deionized water) |
| $AlCl_3.6H_2O$ | 2.0 |
| $CoCl_2.6H_2O$ | 0.8 |
| $KCr(SO_4)_2.12H_2O$ | 0.2 |
| $CuCl_2.2H_2O$ | 0.2 |
| $H_3BO_3$ | 0.1 |
| KI | 2.0 |
| $MnSO_4.H_2O$ | 2.0 |
| $NiSO_4.6H_2O$ | 0.09 |
| $Na_2MoO_4.2H_2O$ | 0.4 |
| $ZnSO_4.7H_2O$ | 0.4 |

EXAMPLE 12

This example describes purification of the restrictocin obtained according to Examples 10 and 11.

(i) Lysis

E. coli. paste was resuspended in lysis buffer [50 mM Tris (hydroxymethyl) aminomethane hydrochloride], 2 mM EDTA, 0.02% Sodium azide, pH 8.2) at between 4–20 ml buffer per g of wet cell paste using a homogeniser (Polytron). The resuspended cells at 4° C. were then lysed by high pressure homogenisation (3 passes through Manton Gaulin homogeniser) or sonication (4×45 sec bursts) and the resulting lysed cell suspension centrifuged at 25,000 g for 20 minutes to yield lysis supernatant and pellet fractions.

Soluble restrictocin was detected as follows. Lysis supernatant was subjected to SDS-PAGE and electroblotted (Matsuidara et al, J. Biol. Chem (1987) 262: 10035-38), a band corresponding to the molecular weight of restrictocin (Approx. 17 KDa) was excised and subjected to N-terminal sequencing on an Applied Biosystems 475 protein sequencer (Applied Biosystems, USA). The resulting sequence confirmed that the protein was restrictocin. Presence of soluble restrictocin was confirmed by the band remaining in the supernatant fraction even after ultracentrifugation (100,000 g for 30 minutes).

The presence of insoluble restrictocin in the lysis pellet was demonstrated by SDS-PAGE electroblotting and sequencing.

(ii) Renaturation

Insoluble restrictocin is recovered from pellet as follows. The resulting pellet is resuspended in phosphate buffered saline (10 mM sodium phosphate, 150 mM sodium chloride, pH 7.4, hereafter abbreviated to PBS) containing 1 mM EDTA and centrifuged at 25000 g for 30 minutes. The resulting washed inclusion body pellet is dissolved in a denaturing buffer (e.g. 6M guanidine hydrochloride/PBS or 8M urea/PBS either of which may contain reductant, e.g. 0.1M beta mercaptoethanol) by stirring slowly at room temperature for 1 hour. The resulting solution is centrifuged at 25000 g for 30 minutes and the supernatant containing the recombinant toxin decanted off.

The solubilised toxin is renatured by controlled removal of the denaturing solution (e.g. by dialysis at 4° C. or by 50 fold dilution) into an appropriate renaturing buffer. Such renaturing buffer may consist of, for example, PBS, or PBS which contains one or more agents which may promote effective renaturation and disulphide bond formation, for example 0.5M arginine, 0.5 mM oxidised and 0.5 mM oxidised glutathione.

Following renaturation and disulphide bond formation, either by dialysis or dilution from denaturing into renaturing buffers, protein precipitate is removed by centrifugation at 25000 g for 30 minutes, and the supernatant containing the soluble toxin decanted off.

(iii) Purification

The soluble toxin containing solution was subsequently purified as outlined below. The pH of the supernatant containing soluble toxin was adjusted to 7.5-8.5 by the addition of dilute sodium hydroxide or hydrochloric acid then was loaded onto a carboxymethyl ion exchange column (such as carboxymethyl Sepharose fast flow from Pharmacia) pre-equilibrated in 50-100 mM Tris/HCl, 2 mM EDTA, 0.02% Sodium azide of the same pH as the supernatant that is loaded. The column was eluted with a linear gradient of 0-0.5M sodium chloride in the buffer used to equilibrate the column. The elution position of the toxin was determined by SDS-PAGE analysis of the column fractions, and those fractions containing the toxin were pooled.

Further purification was achieved by additional chromatography such as dye affinity or hydrophobic interaction chromatography. For example on a dye affinity column (e.g. mimetic green A6XL from Affinity Chromatography Ltd, Cambridge) where the pooled fractions are buffer exchanged into 20 mM Sodium phosphate pH 7.5 by dialysis or diafiltration and any precipitate removed by centrifugation at 40,000 g for 20 minutes. The toxin solution was loaded onto the dye affinity column pre-equilibrated in 20 mM Sodium phosphate pH 7.5, and the flow through solution collected. The column was washed with 20 mM Sodium phosphate pH 7.5 and the wash solution collected. Contaminating proteins bind via adsorption to the dye ligand, the bulk of the toxin remains unbound and elutes in the flow through and wash. The elution position of the toxin was determined by SDS-PAGE analysis of the column fractions and toxin containing fractions pooled.

An alternative or additional purification step to the dye affinity step can be achieved by hydrophobic interaction chromatography (such as Phenyl Sepharose CL-4B from Pharmacia). For example pooled toxin fractions from the ion exchange step are diluted 1:1 v/v with 100% saturated Ammonium sulphate, 20 mM Sodium phosphate, pH 7.5 (final concentration 3M Ammonium sulphate) and the pH adjusted to 7.5 with dilute hydrochloric acid. After incubation at 4° C. for 1 hour any precipitate was removed by centrifugation at 40,000 g for 20 minutes and the supernatant loaded onto the column. The column was washed in 3M Ammonium sulphate, 20 mM Sodium phosphate, pH 7.5 until the 280 nm absorbance of the eluate returns to baseline. The column was eluted with a linear gradient of 3-0M Ammonium sulphate, in 20 mM Sodium phosphate, pH 7.5. The elution position of the toxin was determined by analysis of the column fractions by SDS-PAGE following dialysis to remove Ammonium sulphate.

Further purification can be achieved by additional chromatography such as size exclusion chromatography. For example pooled toxin containing fractions from the dye affinity column were concentrated to 0.2-10 mg/ml by ultrafiltration (Amicon stirred cell) and chromatographed on a size exclusion column (such as for example Sephacryl S-200 HR or Sephacryl S-100HR (Pharmacia)) suitable for the fractionation of globular proteins within the range 8-80 kDa. The column was pre-equilibrated with 20 mM Sodium phosphate, 150 mM Sodium chloride, pH 7.5 and the sample eluted with the same buffer. The elution position of the toxin was determined by SDS-PAGE of column fractions and toxin containing fractions pooled.

(iv) Confirmation of the presence of biologically active restrictocin in crude *E.coli* extracts from Examples 10 and 11

Cell paste was processed as described in (i) and (iii) above. Samples were analysed by SDS-PAGE (FIGS. 3A and 3B) and a putative 17 kDa restrictocin band identified. After lysis the restrictocin partitioned into the soluble and insoluble fractions in approximately equal proportions. The identity of the putative restrictocin band was confirmed by SDS-PAGE electroblotting and N-terminal sequencing of the 17 kDa band from the soluble and insoluble fractions of the Example 10 material on an Applied Biosystems 475 protein sequencer (Applied Biosystems Foster City, U.S.A.). This gave sequence data consistent with the presence of the N-terminus of restrictocin along with other contaminating proteins.

A sample of the lysate supernatant from Example 10 material was centrifuged at 100,000 g for 30 mins and the supernatant subjected to SDS-PAGE, the intensity of the restrictocin band was undiminished and the presence of restrictocin was confirmed by N-terminal sequencing and bioassay (Table 12). The assay for biological activity of ribotoxins is set out in Reference Example C. Samples of whole lysed *E.coli* and the lysate supernatant following centrifugation were assayed for protein synthesis inhibition activity from Example 10 (Table 12) and Example 11 (Table 13) cell paste. The crude extracts showed significant activity. Thus the specific activity of the crude extracts was approximately the same as the absolute specific activity of Aspergillus-derived restrictocin. A control E.coli sonication supernatant gave no activity.

TABLE 12

Bioactivity of crude E. coli extracts from Example 10 cell paste

| Sample | | Restrictocin concentration (ug/ml) | IC50 (ng/ml) |
|---|---|---|---|
| 1 | Aspergillus derived restrictocin[a] | 600 | 0.47 |
| 2 | Aspergillus derived restrictocin[a] | 100 | 0.48 |
| 3 | Whole E. coli sonicate | 10 | 1.13 |
| 4 | Sonication supernatant[b] | 5 | 1.94 |
| 5 | Control E. coli supernatant[c] | — | no activity |
| 6 | Ricin standard[d] | — | 0.224 |

[a] = Aspergillus derived restrictocin was purified as described in U.S. Pat. No. 3,104,208 Olson et al.
[b] = The sonication supernatant was subjected to centrifugation at 100,000 g for 30 minutes and the supernatant assayed.
[c] = Sonication supernatant from E. coli without the restrictocin encoding plasmid, total protein content approximately half that of sample 4 as judged by SDS-PAGE.
[d] = Recombinant Ricin was purified as described in Reference Example B.

The protein concentration of the restrictocin and ricin standards was determined by amino acid analysis (the concentration of all subsequent standards was determined by amino acid analysis). The restrictocin concentration of samples 3 and 4 was estimated by comparison of the 17 KDa band obtained from SDS-PAGE with known amounts of standard proteins run on the same gel (this applies to all subsequent samples unless otherwise stated).

TABLE 13

Bioactivity of crude E. coli extracts from Example 11 cell paste

| Sample | | Restrictocin concentraion (ug/ml) | IC50 (ng/ml) |
|---|---|---|---|
| 1 | Restrictocin standard | 900 | 0.105 |
| 2 | Sonication supernatant | 3 | 0.06 |

Control extracts prepared from E.coli MSD460(pICI0122; as hereinbefore described) not expressing restrictocin (Table 14) did give some activity in the protein synthesis inhibition assay but only when the samples were relatively concentrated (IC50's at dilutions of crude extracts at between 47–195 fold). This background level of protein synthesis inhibition was likely to have been due to components of the E.coli.

In contrast the extracts from E.coli MSD460(pICI 1453) expressing restrictocin (Table 15) gave activity in the assay at much greater dilutions (IC50's at between 7627–15385 fold) confirming the presence in MSD460(pICI 1453) of biologically active soluble restrictocin.

The specific activity of the restrictocin present in the ultracentrifuged lysis supernatant was approximately the same as the absolute specific activity of Aspergillus derived restrictocin (Table 10); thus providing further evidence that the expressed protein was biologically active restrictocin.

TABLE 14

Bioactivity of control E. coli extracts (a)

| Sample | Dilution of extract that inhibited protein synthesis by 50% (IC50) |
|---|---|
| Control whole E. coli lysate | 1/195 |
| Control lysis supernatant | 1/185 |
| Control lysis pellet | 1/47 |

(a) = Control E. coli MSD 460 (pICI0122) containing an expression vector identical to pICI 1453, but which lacks the restrictocin coding sequence grown under identical conditions to Example 11. Cell paste processed as for (i) above.

TABLE 15

Bioactivity of restrictocin expressing E. coli extracts (a)

| Sample | Dilution of extract that inhibited protein synthesis (IC50) by 50% | IC50 ng/ml Restrictocin | IC50 (× 10E-11M) |
|---|---|---|---|
| Whole E. coli lysate | 1/8658 | 23.1 | 135.9 |
| Lysis supernatant | 1/15385 | 1.3 | 7.6 |
| Lysis pellet | 1/7627 | 23.6 | 13.9 |
| Aspergillus derived restrictocin (b) | — | 0.7 | 4.1 |

(a) = E. coli MSD 460 (pICI 1453) containing the restrictocin expression vector grown as described in Example 11. Cell paste processed as for (i) above.

The restrictocin concentration of the samples was estimated by comparison of the intensity of the 17kDa band obtained from SDS-Page with known amounts of purified restrictocin (where the protein concentration had been determined by amino acid analysis) run on the same gel (this applies to all subsequent samples unless stated otherwise).

(b) = Aspergillus derived restrictocin was purified as described in U.S. Pat. No. 3,104,208 Olson et al.

The protein concentration of the Aspergillus derived restrictocin was determined by amino acid analysis (the concentration of all subsequent restrictocin and ricin standards was determined by amino acid analysis).

(v) Chromatographic purification of restrictocin from sonication supernatant

Example 10 cell paste was processed and subjected to chromatography on a carboxymethyl Sepharose fast flow column and then to mimetic green chromatography as described in (iii) above. Restrictocin containing fractions obtained from ion exchange chromatography of Example 11 cell paste material were also subjected to mimetic green chromatography as described in (iii) above.

(vi) Size exclusion chromatography of pooled mimetic green fractions

Figure 4:
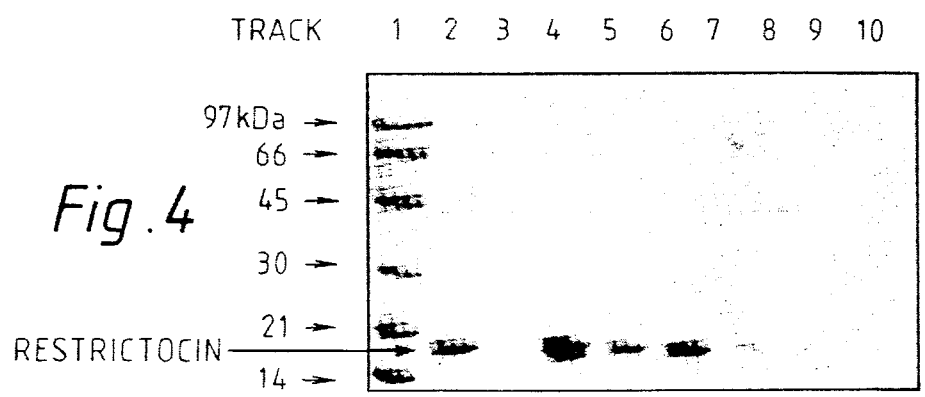

The pooled restrictocin containing fractions obtained from mimetic green chromatography from Examples 10 and 11 cell paste as described in (v) were concentrated by ultrafiltration (Amicon stirred cell YM2 membrane) and subjected to chromatography on a Sephacryl S-100 HR column (Example 10 cell paste material) or on a Sephacryl S-200HR column (Example 11 cell paste material) as described in (iii). Samples of the fractions were analysed by SDS-PAGE (FIG. 4) [Example 11 cell paste material]. The restrictocin eluted with an apparent molecular weight of about 17 kDa, consistent with being monomeric. The restrictocin appeared >98% pure by SDS-PAGE. A sample of the pooled toxin containing fractions was SDS-PAGE blotted and the restrictocin band gave the N-terminal sequence of restrictocin (SEQ. ID. NO. 18) with no other detectable sequence. The full N-terminal sequence of restrictocin is set out in SEQ. ID. NO. 19.

The purified restrictocin was assayed for protein synthesis inhibition activity (Table 16 and Table 17) and had comparable activity to the Aspergillus derived toxin.

TABLE 16

Bioactivity of S-100 purified restrictocin for Example 10 cell paste material

| Sample | | Restrictocin concentration (µg/ml) | IC50 (ng/ml) | IC50 (× 10E-11M) |
|---|---|---|---|---|
| 1 | Aspergillus derived restrictocin | 90 | 1.24 | 7.3 |
| 2 | S100 pooled fractions | 1400 | 1.51 | 8.9 |
| 3 | S100 fraction 27 (contained no restrictocin) | — | no activity | |

*concentration of restrictocin determined by amino acid analysis

TABLE 17

Bioactivity of S-200 purified restrictocin from Example 11 cell paste

| Sample | | Restrictocin concentration (ug/ml) | IC50 (ng/ml) | IC50 (× 10E-11M) |
|---|---|---|---|---|
| 1 | Aspergillus derived restrictocin | 90 | 1.01 | 5.9 |
| 2 | S200 pooled column fractions 20 and 21 | 220 | 0.79 | 4.7 |
| 3 | S200 column fraction 30 (contained no restrictocin) | — | no activity | |

*concentration of restrictocin determined by amino acid analysis

EXAMPLE 12

Restrictocin may also be secreted from *E. coli* at high yields. The coding sequence of restrictocin is removed from pICI 1453 and inserted downstream of the pelB secretion leader in place of the existing gene sequence in vector pICI 1555 which utilizes the araB promoter to drive expression of gene sequences cloned downstream thereof. The constructed vector is then transformed into *E. coli* MSD460 whereupon following growth of the bacteria and induction of gene expression with arabinose, a protein consisting of restrictocin fused to a secretion leader is expressed, and translocated to the cytoplasmic membrane where restrictocin is secreted through that membrane. Whilst measurable quantities of restrictocin can be produced with conventional strains of *E. coli* such as MSD522, significantly greater quantities can be produced using protease deficient strains of *E. coli* such as MSD460 described herein, or strains deficient in the periplasmic protease degP (Strauch and Bekwith (1988) Proc. Nat. Acad. Sci. 85, 1576–1580) or the outer membrane protease ompT (Baneyx and Georgiou (1990) J. Bact. 172, 491–494). It will be appreciated that: other secretion leader sequences, such as the alkaline phosphatase leader or the β-lactamase leader could be used and; other secretion vectors could be used. Engineering *E. coli* to secrete heterologous gene products has been reviewed by J. A. Stader and T. J. Silhavy in Methods in Enzymology 185, Academic Press 1990, edited by D. V. Goeddel.

EXAMPLE 14

This example sets out another method whereby restrictocin can be secreted from *E.coli* at high yields. For example the coding sequence of restrictocin can be cloned into an expression vector such that it is inserted downstream of a secretion leader such as pelB. Engineering *E. coli* to to secrete heterologous gene products has been reviewed by J. A. Stader and T. J. Silhavy in Methods in Enzymology, 185, Academic Press 1990, edited by D. V. Goeddel.

Using the pelB signal sequence to direct secretion of heterologous proteins from *E.coli* has been described in International Patent Publication No. W089/06283 from Ingene. The vector, pRR177-8, which contains the pelB leader and the L6 light chain gene downstream of the lac promoter and which is described in the above patent and deposited on Jan. 12, 1988 under accession number B-18289 in the Agricultural Research Culture Collection (NRLL) (1815 North University St., Peoria, Ill., U.S.A. 61604) can be used as the starting point for expression. There are no convenient restriction (i.e. cloning) sites at the junction of the 3′ end of the pelB signal sequence and the $V_K$ sequence. Therefore, a cloning site is introduced by site-directed mutagenesis. Firstly the DNA sequence around the 3′ end of the pelB sequence must be determined by, for example, using a sequencing primer which anneals to the pelB signal sequence e.g. SEQ ID NO. 20 set out below.

ATGAAATACC TATTGCC

Using the information obtained from sequencing, a mutagenic oligonucleotide is designed for site-directed mutagenesis. The mutagenic oligonucleotide is designed to introduce a NaeI restriction site at the 3′ end of the pelB signal sequence. The subsequent pelB signal sequence and sequence directly downstream is given below. The NaeI sequence is underlined. Cleavage with NaeI generates a blunt ended fragment ending directly at the 3′ end of the pelB signal sequence (see SEQ ID NO: 21).

```
ATG AAA TAC CTA TTG CCT ACG GCA GCC GCT GGA TTG TTA TTA CTC GCT 48
MET Lys Tyr Leu Leu Pro Thr Ala Ala Ala Gly Leu Leu Leu Leu Ala
1               5                   10                  15

GCC CAA CCA GCG ATG GCC GGC...
Ala Gln Pro Ala Met Ala
        20
```

Prior to mutagenesis, a DNA fragment of pRR177-8 containing the pelB sequence (for example, the EcoRI-SalI fragment) is subcloned into a M13mp vector. Mutagenesis is performed using the Oligonucleotide-directed In-Vitro Mutagenesis System Version 2 supplied by Amersham (code RPN-1523). This kit is based on the method of Sayers et al. ((1988) Nucleic Acids Res., 16, p791–802). Following mutagenesis, the fragment is cloned back into pRR177-8 using the same cloning sites to generate a secretion expression vector, pRR177-8-NaeI.

The restrictocin coding sequence can then be cloned into the NaeI site of pRR177-8-NaeI, such that the restrictocin sequence is in frame with the pelB sequence, and such that on expression and secretion the protein is cleaved to generate mature restrictocin. The restrictocin fragment is obtained by digestion of the M13-restrictocin clone (see Reference Example A) with PstI (followed by blunt-ending with T4 DNA polymerase) and then with SalI. This is cloned into the NaeI and SalI sites of pRR177-8-NaeI. The resulting restrictocin secretion vector is used for expression in strains such as E.coli JM103 (ATCC No 39403) or E. coli MC1061 (ATCC No 53338) following the protocol described in section 6.4.3. patent WO89/06283. If necessary, expression levels could be further increased by making a derivative of the restrictocin secretion vector as described in section 6.4.2. of the above patent.

Whilst measurable quantities of restrictocin should be produced with the conventional strains of E.coli, significantly greater quantities are produced using protease deficient strains of E. coli such as MSD460 described herein, or strains deficient in the periplasmic protease degP (Strauch and Bekwith (1988) Proc. Nat. Acad. Sci. 85, p1576-1580) or the outer membrane protease ompT (Baneyx and Georgiou (1990) J.Bact. 172, 491-494).

Reference Example B

The example describes the purification of r-ricin a from E. coli under optimal fermentation conditions, r-ricin A accumulates as a soluble cytosolic protein. This protein was recovered by breakage of the cells (homogenization) in a buffer which promotes the stability of r-ricin A. This unit operation was performed on live cells at harvest to ensure solution stability of the product. r-Ricin A was recovered from the homogenate by removal of solids (cell debris) by centrifugation. In order for this procedure to be scaled-up the debris was flocculated with an agent (polythene imine) which also precipitates the bulk of the nucleic acid present in the extract. The centrifuge supernatant was then sterile filtered, concentrated by cross flow filtration and the protein precipitated with ammonium sulphate. The ammonium sulphate precipitate was stored frozen at −70° C.

r-Ricin A has an isoelectric point of 7.3 well above the isoelectric point of many other E. coli proteins. The product may therefore be conveniently purified by ion-exchange chromatography. All the recovery and chromatography steps were performed under conditions which promote r-ricin A stability: temperature <15° C., presence of dithiothreitol to maintain the free thiol in a reduced state and EDTA to reduce air oxidation and proteolysis.

Recovery of r-Ricin A

The cells were collected from the fermentation broth using a continuous disc stack intermittent discharge separater. The broth (50l from 2×25l fermentation) was initially transferred from the fermenters to a 50l trundle tank and transported to a contained system consisting of a number of holding tanks connected to the separater and homogenizer.

The trundle tank was connected to this system and the broth pumped through the centrifugal separater at a flow rate of 40l/h. The discharge rate was adjusted to that the centrifuge supernatant was clear by visual inspection of an eyeglass in the supernatant discharge line. The supernatant was collected in a kill tank containing 20l of 0.1M sodium hydroxide sanitizing solution prior to disposal. The cells were resuspended in 40l of Buffer A (see below) and prechilled to 8° C. in the solids receiver vessel. The suspended cells were then transferred back to the trundle tank via the homogenizer adjusted to a working pressure of 600 bar. The resulting homogenate (60l) was chilled to <20° C. and make 0.5% with respect to polythenemine by the addition of 2.5l of a 10% (v/v) solution. The suspension was allowed to flocculate for 10 min before transfer to the Holding Tank via the centrifugal separater. The clear supernatant was then sterilized by purifying through a depth filter and a positively charged 0.2μ membrane filter.

Ammonium Sulphate Precipitation

The sterile clarified supernatant was concentrated to a volume of 12l using a spiral cartridge cross flow filtration device and the solution brought to 40% saturation by the addition of 2.9 kg of solid ammonium sulphate crystals. The solution was allowed to flocculate by gentle stirring overnight at 15° C. and then centrifuged using the continuous flow centrifuge. The discharged slurry was stored at 70° C. until required for further processing.

Resolubilization and Desalting

The ammonium sulphate precipitate was thawed in the presence of 14l of Buffer B (see below). After 30 min the suspension was clarified by centrifugation and desalted by diafiltration against 70l of Buffer B and the conductivity checked that it had been reduced to below 3MS/cm. The desalted solution was claified further by centrifugation and processed immediately.

Anion Exchange Chromatography

The desalted solution was slowly added to a batch chromatography tank containing 2 kg of DEAE-cellulose which had been equilibrated with 60l of Buffer B. After stirring for 6.5 h the unbound r-ricin A solution was pumped from the bottom of the tank through an 11.3 cm diam × 10 cm column of packed and equilbrated DEAE-cellulose at a flow rate of 80 ml/min. The bulk of the r-ricin A did not bind and was collected in a stainless steel vessel.

Cation Exchange Chromatography

The r-ricin A solution was adjusted to pH 5.5 with 1M orthophosphoric acid and applied to a 10 cm diameter×10 cm column of carboxymethyl agarose equilibrated with 10l of Buffer C (see below). The r-ricin A bound to this column and after washing with 10l of Buffer C was eluted with Buffer D (see below). The pure r-ricin A eluted as a single peak which was collected and stored at 4° C. as a sterile solution until required for further processing. The r-ricin A is stable under these conditions for up to 2 months.

Raw Materials and Equipment

| | | |
|---|---|---|
| Anion exchanger | DE-52 | Whatman Biochemicals |
| | DEAE Cellulose | |
| Cation exchanger | CH/Sepharose | Pharmacia |
| Buffer A | 50 mM sodium dihydrogen orthophosphate | |
| | 25 mM ethylene diamine tetra acetic acid | |
| | 5 mM benzamidine | |
| | 2 mM dithiothreitol | |
| | pH 6.3 with 5N sodium hydroxide | |
| Buffer B | 50 mM sodium dihydrogen orthophosphate | |

| | -continued | |
|---|---|---|
| | 25 mM ethylene diamine tetracetic acid<br>2 mM dithiothreitol<br>pH 6.3 with 5N sodium hydroxide | |
| Buffer C | 25 mM sodium dihydrogen orthophosphate<br>5 mM ethylene diamine tetra acetic acid<br>2 mM dithiothreitol<br>pH 5.5 with 5N sodium hydroxide | |
| Buffer D | 25 mm sodium dihydrogen orthophosphate<br>5 mM ethylene diamine tetracetic acid<br>2 mM dithiothreitol<br>100 mM sodium chloride<br>pH 5.5 with 5N sodium hydroxide | |
| Centrifuge | Westphalia CSA-1<br>Disk stack centrifuge | Westphalia |
| Homogenizer | APV-Schroeder<br>Lab 60/60 homogenizer | APV |
| Filter | AM1 0057P Depth Filter<br>AB1 NFZP-Posidyne<br>membrane filter | Pall |
| Batching Tank<br>Batch chromatography<br>tank | 701 Pharmacia | Pharmacia |
| DE-Column | Bioprocess 113 | Pharmacia |
| CM Column<br>Pharmacia | K100/50 | |

REFERENCE EXAMPLE C

This example describes a biological assay for ribotoxins. The aim was to establish conditions under which samples could be tested for biological activity in a cell-free in vitro protein synthesis assay.

Rabbit reticulocyte lysates are prepared according to the method of Allen and Schweet (J Biol Chem (1962), 237, 760-767). The assay demonstrates inhibition of protein synthesis in a cell-free system by a lack of incorporation of $^{14}C$-labelled leucine into newly synthesised protein.

The Assay Protocol

Stock solution: 1 mM amino acid mix minus leucine. A solution containing all L-amino acids at 1 mM except leucine (adjusted to pH 7.4 with NaOH and stored at −70° C.).

Soln. A
- 40 mM Magnesium acetate
- 2M Ammonium acetate
- 0.2M Tris
- (pH 7.4 with HCl, stored 4° C.)

Soln. B
- adenosine triphosphate (Sigma A5394) 246 mg/ml
- guanosine triphosphate (Sigma G8752) 24.4 mg/ml Assay mix
- 1 ml Amino acid mixture
- 1 ml Soln. A
- 0.1 ml Soln. B
- 103 mg Creatine phosphate
- 1 mg Creatine kinase
- 510 μl $H_2O$
- 600 μl (60 μCi) L-$^{14}C$-leucine (New England Nuclear, NEC-279E)

Reaction mix
- Test sample 25 μl
- Assay mix 12.5 μl
- Rabbit reticulocyte lysate 25 μl
- Blank solution is 2 mg/ml bovine serum albumin(-BSA) in phosphate buffered saline(PBS)
- All assays are performed in duplicate
- 12.5 μl of assay mix placed in sterile glass tubes
- 25 μl of BSA in PBS added to each of first four tubes for blanks
- 25 μl of test samples added to rest of tubes
- 1 ml 0.1M potassium hydroxide added to first two tubes (background blank)
- Tubes equilibrated to 28° C. in a water bath
- 25 μl of rabbit reticulocyte lysate (allowed to thaw from liquid nitrogen temperature) were added to each tube at 20 second intervals. When first tube had incubated for 12 minutes, 1 ml 0.1M KOH was added to each tube again at 20 second intervals to allow all tubes to have 12 minutes incubation. Two drops of 20% hydrogen peroxide were added to each tube followed by 1 ml of 20% trichloroacetic acid (TCA).

Tubes were mixed and allowed to stand for at least 1 hour, or overnight, at 4° C. The precipitates were filtered on to 2.5 cm glass fibre circle (GFC) discs, washed with 3×4 ml of 5% TCA, transferred to scintillation vials and 10 ml scintillant (Ready-Solv. MP, Beckman) added. After 1 hour the vials were shaken and counted.

Establishment of Technique for use with *E.coli* Lysates 10 ml L-broth overnight cultures are grown at 37° C. 400 μl aliquots are pelleted at 13000 rpm for 30 seconds and most of the supernate decanted.

The pellets are subjected to 2 rounds of rapid freezing in solid carbon dioxide/ethanol followed by thawing at 37° C. 12 μl of 25% sucrose in 50 mM Tris HCl pH 8.0 is added followed by 4 μl of a 10 mg/ml solution of lysozyme.

After incubation on ice for 15 minutes, 8 μl of 0.25M EDTA is added and incubation continued for 15 minutes. Lysis is brought about osmotically by diluting the samples to 400 μl with water. This procedure produces viable cell counts of 80-100 per ml.

When a 25 μl aliquot of this lysate is added into the assay reaction mix, the level of incorporation of $^{14}C$-leucine into newly synthesised protein is ~10% of the blank without lysate. The result clearly showed that a minimum 16-fold dilution was necessary to reduce the effect of the lysate to equal that of the blank.

In order to be as confident as possible that lysis of *E.coli* and *E.coli* lysates would not compromise ribotoxin toxicity, 2 control assays were performed. The first added ribotoxin to a 16X diluted *E.coli* cell pellet so as to give a final concentration of 8 ng/ml in the assay mix after cell lysis. Both these controls showed no deleterious affect from the lysates or the lysis procedure on the inhibitory action of ribotoxin.

These techniques were used to verify the synthesis of biologically active ribotoxin.

The assay for biological activity of ribotoxins can also be carried out by following literature methods as set out below.

Rabbit reticulocyte lysates were prepared according to the method of Allen and Schweet (J. Biol. Che. (1962), 237, 760-767). The assay is capable of demonstrating an inhibition of protein synthesis (14C labelled leucine incorporation into newly synthesised protein) in a cell-free assay).

Assay protocol:

The assay was carried out essentially as described by Stirpe et al (Biochem J, 195, 399-405, 1981). The samples were incubated for 30 minutes at room temperature, the reaction stopped by addition of 500 μl of 0.1M potassium hydroxide and the amount of radioactivity incorporated into TCA precipitated protein was measured by scintiallation counting. Results were expressed as a percentage of radioactivity incorporated into control samples incubated in the absence of ribotoxin and the IC50 was calculated from the dose response curves as the concentration of ribotoxin (or amount of E.coli. preparation) required to reduce the 14C-leucine incorporation by 50%.

---

We claim:

1. A method for producing the ribotoxin restrictocin which comprises culture of the host *E. coli* transformed with an expression vector encoding the ribotoxin wherein upon expression the restrictocin is accumulated intracellularly.

2. A method according to claim 1 in which the ribotoxin is accumulated intracellularly under any of the following conditions:
    a) the host is protease deficient and/or;
    b) degradation of the expressed ribotoxin is suppressed after culture of the procaryotic host by:
        i) protease inhibitors and/or;
        ii) rapid processing and/or;
        iii) processing at chilled temperatures.

3. The process according to claim 1 in which the host is *E. coli* MSD460, deposited as NCIMB No. 40469.

4. The process according to claim 1 in which the host is *E. coli* MSD199, deposited as NCIMB No. 40468 or *E. coli* MSD500, deposited as NCIMB No. 40470.

* * * * *